(12) United States Patent
Sugihara et al.

(10) Patent No.: US 8,410,062 B2
(45) Date of Patent: *Apr. 2, 2013

(54) COLLAGEN PEPTIDE, DIPEPTIDE AND MALADY INHIBITOR

(75) Inventors: Fumihito Sugihara, Osaka (JP); Naoki Inoue, Osaka (JP); Seiko Koizumi, Osaka (JP); Chinfang Liu, Tochigi (JP); Hajime Takasaki, Osaka (JP); Hisayuki Kobayashi, Osaka (JP); Hiroshi Mano, Saitama (JP); Sachie Nakatani, Saitama (JP); Masahiro Wada, Saitama (JP)

(73) Assignee: Nitta Gelatin Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/523,438

(22) Filed: Jun. 14, 2012

(65) Prior Publication Data

US 2012/0258919 A1    Oct. 11, 2012

Related U.S. Application Data

(62) Division of application No. 12/443,298, filed on Mar. 27, 2009, now Pat. No. 8,227,424.

(30) Foreign Application Priority Data

Sep. 30, 2008    (JP) ................................. 2008-254552

(51) Int. Cl.
*A61K 38/05*    (2006.01)
(52) U.S. Cl. .................... 514/21.91; 514/16.9
(58) Field of Classification Search ............... 514/21.9
See application file for complete search history.

(56) References Cited

U.S. PATENT DOCUMENTS

| | | | |
|---|---|---|---|
| 3,267,006 A | 8/1966 | Hakim | |
| 5,972,623 A | 10/1999 | Krane et al. | |
| 6,521,643 B1 | 2/2003 | Tomishima et al. | |
| 6,645,948 B2 | 11/2003 | Petito et al. | |
| 8,227,424 B2 * | 7/2012 | Sugihara et al. | 514/21.91 |

FOREIGN PATENT DOCUMENTS

| | | |
|---|---|---|
| JP | 2002-51734 | 2/2002 |
| JP | 2002-125638 | 5/2002 |
| JP | 2002-255847 | 9/2002 |
| JP | 2003-48850 | 2/2003 |
| WO | 87/05219 | 9/1987 |
| WO | 99/06840 | 2/1999 |
| WO | 02/098449 | 12/2002 |
| WO | 2004/110470 | 12/2004 |
| WO | 2005/116086 | 12/2005 |

OTHER PUBLICATIONS

Waters et. al, Purification and Characterization of an Iminopeptidase from the Primary Leaf of Wheat—*Triticum aestivum* L., Plant Physiol. 73, 1048-1054 (1983).*
Samonina et. al. Glycoproline family: review on bioactivity and possible origins, Pathophysiology (8) 229-234 2002.*
Shigemura, Y. et al., Influence Exerted by Food-Derived Main Collagen Peptides (Pro-Hyp, Hyp-Gly) on Proliferation of Mice's Skin Fibroblasts, Abstracts of Lectures at Lecture Meeting of Kansai Branch of Japanese Agricultural Chemical Society, published Sep. 10, 2008, vol. 456, p. 28.
Yamato, R. et al., Effects of Collagen Tripeptide on Osteoarthrosis of Knees, Abstracts of Lectures at Large Meeting of Japanese Nutritional Food Science Society, published 2007, vol. 61, p. 233.
Yamamoto, M. et al., Effects of Collagen Peptide Ingestion on Bone Metabolism of Ovary-Enucleated Model Rats having Osteoporosis, Abstracts of Lectures at Large Meeting of Japanese Nutritional Food Science Society, published 2007, vol. 61, p. 233.
Samonina, G. et al., Glyproline peptide family: review on bioactivity and possible origins, Pathophysiology (8) 229-234 (2002).
Lee, S. et al., Pressure ulcer healing with a concentrated, fortified, collagen protein hydrolysate supplement: a randomized controlled trial, Advances in Skin & Wound Care, Mar. 2006, vol. 19(2), pp. 92-96, Abstract.
Singaporean Office Action dated Mar. 9, 2012 in corresponding SG Application No. 201100714-3.
Supplementary European Search Report dated Nov. 19, 2012, from the EP Patent Office in corresponding EP Application No. 08877173.8.

* cited by examiner

*Primary Examiner* — Christina Bradley
*Assistant Examiner* — Jeanette Lieb
(74) *Attorney, Agent, or Firm* — Roylance, Abrams, Berdo & Goodman, L.L.P.

(57) ABSTRACT

A problem that the present invention is to solve is to provide: a main body of a peptide molecule which is effective for inhibition of various maladies such as osteoporosis, osteoarthritis and pressure ulcer, particularly, a dipeptide which is easy to absorb into a body in an intestine; a collagen peptide which comprises the dipeptide as an essential dipeptide; and a malady inhibitor which comprises the dipeptide as an essential effective component. As a means of solving such a problem, a collagen peptide according to the present invention is characterized by comprising a dipeptide having a structure of Hyp-Gly as an essential dipeptide. A dipeptide according to the present invention is characterized by having a structure of Hyp-Gly. A malady inhibitor according to the present invention is characterized by comprising a dipeptide having a structure of Hyp-Gly as an essential effective component.

6 Claims, No Drawings

COLLAGEN PEPTIDE, DIPEPTIDE AND MALADY INHIBITOR

CROSS REFERENCE TO RELATED APPLICATION

This application is a divisional application of Ser. No. 12/443,298, filed Mar. 27, 2009 now U.S. Pat. No. 8,227,424.

TECHNICAL FIELD

The present invention relates to a collagen peptide, a dipeptide and a malady inhibitor. In detail, the invention relates to: a collagen peptide comprising a dipeptide having a specific structure as an essential dipeptide; a dipeptide having a novel structure; and a malady inhibitor which comprises the dipeptide as an essential effective component and is effective for inhibition (in the present invention, the term "inhibition" includes both of a meaning as "prevention" to inhibit occurrence of symptoms and a meaning as "curing" to inhibit caused symptoms) of such as osteoporosis, osteoarthritis and pressure ulcer.

BACKGROUND ART

The osteoporosis means a condition where decrease of the absolute amount of a bone is caused, but where no qualitative change of the bone is involved. A bone is constantly absorbed and formed, and if a difference between the absorption ratio and the formation ratio is made so that the bone formation becomes negative in balance, then osteoporosis occurs. The bone absorption is made by osteoclasts, and as differentiation and activation of the osteoclasts become greater, the bone absorption ratio becomes higher. On the other hand, the bone formation is made by osteoblasts, and as differentiation and activation of the osteoblasts become greater, the bone formation ratio becomes higher.

The osteoarthritis is a malady such that a chronic regressive change and a chronic proliferative change occur simultaneously to a joint to thus change the form of the joint. As a result, an articular cartilage is gradually abraded and lost, so that a bone becomes exposed. In the articular cartilage, there is not any vascular system, and particularly, articular sliding part cartilage cells and rib cartilage tissue are more difficult to repair or regenerate than bone tissue where there is a vascular system. Particularly, if the bone tissue which supports the articular cartilage becomes sparse (osteoporosis), then the function of the articular part is hindered, so that the osteoarthritis is caused.

The pressure ulcer means a condition where during long-term lying in bed, skin and soft part tissue in a place where a bone is projected undergo circulation disable due to long-term press between the bone and the bed to thus fall into necrosis.

As an effect of a peptide on the above symptoms, an effect on the osteoarthritis is reported. For example known are the following: a joint-strengthening drink comprising a collagen peptide and a glucosamine salt as effective components and having a pH of 2 to 5 (refer to patent document 1 below); an improving drug for rheumatoid arthritis or the osteoarthritis which agent is obtained by decomposing a collagen component or a gelatin component using a collagenase enzyme and comprises a tripeptide of Gly-X-Y in amino acid sequence as an effective component (refer to patent document 2 below); and an oral articular disable curing drug or functional food being characterized by comprising: at least one member selected from the group consisting of collagen and collagen peptides; an amino saccharide; and at least one member selected from the group consisting of mucopolysaccharides and uronic acid (refer to patent document 3 below).

[Patent document 1]
JP-A-2002-125638
[Patent document 2]
JP-A-2002-255847
[Patent document 3]
JP-A-2003-048850

DISCLOSURE OF THE INVENTION

Problems that the Invention is to Solve

However, the above prior arts only disclose that collagen, a collagen peptide (which is a mixture of various peptide molecules) or a specific tripeptide is effective for prevention or curing of the osteoarthritis. A peptide structure which is effective for prevention or curing of maladies in the broad meaning including not only the osteoarthritis, but also such as osteoporosis and pressure ulcer has not yet been known.

Thus, problems that the present invention is to solve are: to, from viewpoint different from prior arts, worm out a main body of a peptide molecule which is effective for inhibition of various maladies such as osteoporosis, osteoarthritis and pressure ulcer, particularly, a dipeptide which is easy to absorb into a body in an intestine and is novel; and to provide: a malady inhibitor which comprises the dipeptide as an essential effective component; and a collagen peptide which comprises the dipeptide as an essential dipeptide.

Means of Solving the Problems

The present inventors diligently studied to solve the above problems. As a result, they have completed the present invention by finding out that a dipeptide having a structure of Hyp-Gly discovered newly by the present inventors is easy to absorb into a body in an intestine and works as an effective component of a malady inhibitor, specifically, for example, inhibits differentiation and activation of osteoclasts, promotes differentiation and activation of osteoblasts, and inhibits degeneration of cartilage cells to thus adjust their differentiation, and that the above dipeptide is effective for inhibition of osteoporosis and osteoarthritis, and further that this dipeptide recovers the amount of tropocollagen in skin dermis to thus also inhibit pressure ulcer, and by confirming these facts.

That is to say, a collagen peptide according to the present invention is characterized by comprising a dipeptide having a structure of Hyp-Gly as an essential dipeptide.

A dipeptide according to the present invention is characterized by having a structure of Hyp-Gly.

A malady inhibitor according to the present invention is characterized by comprising a dipeptide having a structure of Hyp-Gly as an essential effective component.

Effects of the Invention

The present invention can effectively inhibit symptoms of such as osteoporosis, osteoarthritis and pressure ulcer.

BEST MODE FOR CARRYING OUT THE INVENTION

Hereinafter, detailed descriptions are given about the collagen peptide, dipeptide, and malady inhibitor according to the present invention. However, the scope of the present invention is not bound to these descriptions. And other than the following illustrations can also be carried out in the form of appropriate modifications of the following illustrations within the scope not departing from the spirit of the present invention.

[Dipeptide, Collagen Peptide]

The dipeptide according to the present invention has a structure of Hyp-Gly.

The collagen peptide according to the present invention comprises the aforementioned dipeptide as an essential dipeptide. As mentioned below, this collagen peptide can, for example, be obtained by enzymatically treating collagen or gelatin.

In the dipeptide having a structure of Hyp-Gly, the hydroxyproline unit and/or the glycine unit may be chemically modified, and as to the hydroxyproline unit, its hydroxy group may be chemically modified.

In the above way, in the present invention, the "dipeptide having a structure of Hyp-Gly" encompasses both a chemically modified one and a non-chemically-modified one. In addition, hereinafter, the "dipeptide having a structure of Hyp-Gly" may simply be referred to as "Hyp-Gly" (such a reference is similarly applied also to other peptides).

In the case where the Hyp-Gly is chemically modified, it can be made soluble in the range of weak acidity to neutrality, and such as enhancement of compatibility with the below-mentioned other effective components can also be expected. Specifically, as to the hydroxyl group of the hydroxyproline residue, chemical modifications such as O-acetylation can be cited, and as to the α-carboxyl group of the glycine residue, chemical modifications such as esterification and amidation can be cited. Proper chemical modifications may be selected according to such as the kinds of the below-mentioned other effective components.

The aforementioned Hyp-Gly can, for example, as mentioned below, obtained by enzymatically treating collagen or gelatin in two separated steps or being synthesized from amino acids. As to the chemical modification, publicly known means as mentioned below can be cited. However, the dipeptide according to the present invention may be obtained by methods other than these methods, for example, by a method in which primary enzymatic treatment is omitted in place of the below-mentioned two-step enzymatic treatment method or by a method in which primary enzymatic treatment and secondary enzymatic treatment are carried out simultaneously.

<Two-Step Enzymatic Treatment of Collagen or Gelatin>

The collagen peptide comprising the Hyp-Gly can be obtained by two-step enzymatic treatment where collagen or gelatin is subjected to primary enzymatic treatment by a conventional method and then subjected to secondary enzymatic treatment by a reaction with an enzyme having hydroxyprolidase activity.

If this two-step enzymatic treatment is carried out, then a peptide having a comparatively large molecular weight which is useful for inflammation relaxation of bone or cartilage tissue through oral immunotolerance mechanism is formed by the primary enzymatic treatment, and, for example, in the case of a peptide having a structure of x-Hyp-Gly (x denotes a residue of an amino acid other than proline), a peptide bond between the Hyp-Gly residue and the x residue (peptide bond derived from the amino group of the Hyp and the carboxyl group of the x) is cleaved by the secondary enzymatic treatment to thus form the Hyp-Gly.

Although not especially limited, examples of the aforementioned collagen include collagens derived from mammals such as cattle and pigs and collagens derived from fish such as sharks and sea breams, and these can be obtained from such as bone and skin parts of the mammals and bone, skin and scale parts of the fish. Specifically, prior publicly known treatments such as degreasing and decalcifying treatments and extraction treatment may be applied to such as the aforementioned bones, skin and scales.

The aforementioned gelatin can be obtained by treating the aforementioned collagen by prior publicly known methods such as hot water extraction.

The enzyme being used in the aforementioned two-step enzymatic treatment of collagen or gelatin is not especially limited. However, if such as cases where the dipeptide being obtained is utilized for such as specific health foods are taken into consideration, it is preferable to use enzymes other than enzymes derived from pathogenic bacteria.

As treatment conditions of the primary enzymatic treatment, for example, 0.1 to 5 weight parts of an enzyme per 100 weight parts of collagen or gelatin can be used to carry out the treatment at 30 to 65° C. for 1 to 72 hours.

The average molecular weight of the collagen peptide obtained by the above primary enzymatic treatment of collagen or gelatin is favorably in the range of 200 to 2000, more favorably 200 to 1800. If the average molecular weight is in the aforementioned range, it can be said that a dipeptide having a comparatively large molecular weight is sufficiently formed.

After the primary enzymatic treatment, if necessary, the enzyme may be deactivated. In this case, the deactivation temperature is, for example, in the range of 70 to 100° C.

The enzyme being used in the aforementioned primary enzymatic treatment is not especially limited, if it is an enzyme which can cleave a peptide bond of collagen or gelatin. However, usually, an enzyme which is called proteolytic enzyme or protease is used. Specifically, examples thereof include collagenase, thiol protease, serine protease, acidic protease, alkaline protease, and metal protease, and these can be used alone respectively or in combinations with each other. As the aforementioned thiol protease, there are known such as chymopapain, papain, bromelain and ficin derived from plants, and cathepsin and calcium-dependent protease derived from animals. In addition, as the aforementioned serine protease, there are known such as trypsin and cathepsin D, and as the aforementioned acidic protease, there are known such as pepsin and chymotrypsin.

Furthermore, in the secondary enzymatic treatment, for example, an enzymatic reaction is made using an enzyme having hydroxyprolidase activity and prolirase activity derived from *Aspergillus*. By this reaction, the Hyp-Gly which is not included in the primary enzymatic treatment product is formed.

As treatment conditions of the secondary enzymatic treatment, for example, 0.01 to 5 weight parts of an enzyme per 100 weight parts of the primary enzymatic treatment product can be used to carry out the treatment at 30 to 65° C. for 1 to 72 hours.

The average molecular weight of the collagen peptide obtained by the above secondary enzymatic treatment is favorably in the range of 200 to 1500, more favorably 200 to 900. This secondary enzymatic treatment makes it the main object to form the Hyp-Gly and is favorably carried out so that a comparative large peptide among collagen peptides obtained by the primary enzymatic treatment will not excessively be hydrolyzed and so that the collagen peptide will fall in the aforementioned average molecular weight range.

After the secondary enzymatic treatment, the enzyme needs to be deactivated. The deactivation temperature is, for example, in the range of 70 to 100° C.

A hydrolyzate obtained by the aforementioned two-step enzymatic treatment or a fermentation product obtained by the aforementioned two-step enzymatic treatment and the fermentation is a mixture comprising another amino acid or peptide component besides the Hyp-Gly. Therefore, in the case where the Hyp-Gly or its salt is obtained, if necessary, fractionation or purification may be carried out. The method for the fractionation or purification is not especially limited. For example, the fractionation or purification may be carried out by prior publicly known methods such as ultrafiltration, various liquid chromatography (e.g. gel-filtration chromatography, ion-exchange chromatography, reversed-phase chromatography, and affinity chromatography), and methods comprising their combinations. Specifically, for example, the fractionation or purification can be carried out in the following way. That is to say, first of all, about 2 g/10 mL of the aforementioned hydrolyzate or fermentation product are separated into two, and they are sequentially charged into an ion-exchange column (e.g. DEAE TOYOPEARL 650M column (produced by TOSOH Corporation), SP TOYOPEARL 650M column (produced by TOSOH Corporation)), and a void volume fraction eluted with distilled water is recovered. Next, the recovered fraction is charged into a column (e.g. SP TOYOPEARL 650M column (produced by TOSOH Corporation), DEAF TOYOPEARL 650M column (produced by TOSOH Corporation)) having an ion-exchange group reverse to the aforementioned ion-exchange column, and a void volume fraction eluted with distilled water is recovered. Next, this fraction is charged into a gel filtration column (e.g. SEPHADEX LH-20 column (produced by Pharmacia Co., Ltd.)), and elution is made with a 30% aqueous methanol solution, so that a fraction corresponding to a position where the Hyp-Gly which is a chemical synthetic product is eluted is recovered. As to this fraction, it is provided to a high performance liquid chromatography (HPLC) equipped with a reversed-phase column (e.g. µBondasphere 5 µC18 300 Å column (produced by Waters Co., Ltd.)) to make fractionation by a linear concentration gradient of a 32% or less aqueous acetonitrile solution containing 0.1% trifluoroacetic acid. Then, an Hyp-Gly fraction recovered is vacuum-dried to solid, so that a high-purity Hyp-Gly can be obtained.

<Synthesis from Amino Acid>

An Hyp-Gly can be synthesized from an amino acid.

As methods for the synthesis of the Hyp-Gly, there are generally (1) a solid-phase synthesis method and (2) a liquid-phase synthesis method (e.g. refer to JP-A-2003-183298), and in the former case, further (A) a Fmoc method and (B) a Boc method are known. However, the Hyp-Gly may be synthesized by any method.

As an example, the solid-phase method is hereinafter explained in detail.

The synthesis can be carried out by a publicly known solid-phase synthesis method in which hydroxyproline is fixed onto a supporting polystyrene, and a Fmoc group or a Boc group is used for protection of an amino group. That is to say, beads of a polystyrene polymer gel of about 0.1 mm in diameter of which the surface is modified with an amino group is used as a solid phase, and glycine is bonded (peptide-bonded) to hydroxyproline (of which the amino group is protected by the Fmoc (fluorenyl-methoxy-carbonyl) group) by a dehydration reaction using diisopropylcarbodiimide (DIC) as a condensing agent, and then the solid phase is well washed with a solvent to remove such as residual glycine. Thereafter, the protecting group of the hydroxyproline residue which is bonded to the solid phase is removed (deprotected), so that the Hyp-Gly can be synthesized.

<Chemical Modification>

The Hyp-Gly may be a chemically modified one. To specific means and treatment conditions of the chemical modification, conventional chemical modification techniques for peptides are applied.

As to chemical modification of a hydroxyl group of the hydroxyproline residue, for example, the O-acetylation can be carried out by making anhydrous acetic acid act in water solvent or in a non-water solvent.

As to chemical modification of an α-carboxyl group of the glycine residue, for example, the esterification can be carried out by passing a dry hydrogen chloride gas after suspending into methanol, and the amidation can be carried out by making such as carbodiimide act.

As other specific examples of the chemical modification, chemical modification techniques as disclosed in such as JP-B-62-044522 and JP-B-05-079046 can be applied.

[Malady Inhibitor]

The malady inhibitor according to the present invention comprises a dipeptide having a structure of Hyp-Gly as an essential effective component. As examples of the malady inhibitor, there can favorably be cited such as osteoporosis inhibitors, osteoarthritis inhibitors and pressure ulcer inhibitors.

The malady inhibitor according to the present invention comprises the dipeptide according to the present invention as an effective component, and besides, the malady inhibitor according to the present invention may be that which comprises the dipeptide according to the present invention as an effective component wherein the dipeptide is contained in the collagen peptide according to the present invention. Then, in this case, the mode may be not only that the aforementioned malady inhibitor comprises an Hyp-Gly chemically synthesized from an amino acid or an Hyp-Gly isolated from a collagen peptide which is a hydrolyzate of collagen or gelatin, but also that the aforementioned malady inhibitor comprises an Hyp-Gly left as it is in the form of a collagen peptide without isolating an Hyp-Gly from the aforementioned collagen peptide. In this way, the malady inhibitor according to the present invention is that which comprises the dipeptide according to the present invention as an effective component, including the mode that an Hyp-Gly left as it is a collagen peptide is made contained, and it is also possible to jointly use these dipeptides, including the case where a dipeptide is used in the form of a collagen peptide.

The aforementioned Hyp-Gly is favorably contained in a ratio of not less than 0.001 weight part, more favorably not less than 0.01 weight part, to the entirety of the aforementioned malady inhibitor according to the present invention. In the case of less than 0.001 weight part, there is a possibility that the effects of the present invention are not sufficiently displayed.

Furthermore, in the case where the malady inhibitor according to the present invention is used by directly injecting it into a diseased part, the content of the aforementioned Hyp-Gly is favorably not less than 1 mmol/L.

The malady inhibitor according to the present invention may be that obtained by diluting the Hyp-Gly with such as physiological saline, and in this case, the effects of the present invention can be sufficiently obtained, but other effective components or components for drug preparation may fitly be made contained besides the aforementioned Hyp-Gly within the range not damaging the effects of the present invention.

The aforementioned other effective components are exemplified by such as glucosamine and/or its salts and chondroitin sulfate. These can be used alone respectively or in combinations with each other. Above all, the glucosamine and/or its salts are favorable since they have a function to enhance the malady-inhibiting effect of the Hyp-Gly.

In addition, peptides or amino acids other than the Hyp-Gly may be contained as the aforementioned other effective components. For example, a peptide having a comparatively large molecular weight is useful since, upon such as chronic rheumatic arthritis, it has an effect to relax inflammation of bone or cartilage tissue by oral immunotolerance mechanism. In order for the peptides or amino acids other than the Hyp-Gly to be made contained, for example, collagen or gelatin is hydrolyzed to obtain a collagen peptide containing the Hyp-Gly, and then this collagen peptide is used intactly without isolating the Hyp-Gly therefrom.

Furthermore, as the aforementioned other effective components, such as calcium or saccharide rearrangement hesperidin can be used for the purpose of promotion of bone salt deposition, and such as vitamin C can also be used for the purpose of such as promotion of synthesis and deposition of collagen.

As the amount of the aforementioned other effective components, they may be used favorably in a ratio of 0.001 to 20 weight parts, more favorably 0.01 to 20 weight parts, to the entirety of the malady inhibitor. Particularly, the amount of the glucosamine and/or its salts is favorably in a ratio of 5 to 15 weight parts to the entirety of the malady inhibitor. In the case of less than 5 weight parts, there is a possibility that the effect of enhancing the effects of the Hyp-Gly is not sufficiently displayed. In the case of more than 15 weight parts, there is a possibility of excessive ingestion since they are discharged into urine or excrement.

As the components for drug preparation, for example, forming materials such as crystalline cellulose can be used, and an appropriate amount may be set according to the form.

Examples of modes for using the malady inhibitor according to the present invention include modes such as ingestion by oral administration and direct injection into diseased parts. The Hyp-Gly is rapidly absorbed in an intestine and is little decomposed into amino acids. Therefore, the ingestion by oral administration is favorable.

In the case of the oral administration, by prior publicly known methods, a mixture of the Hyp-Gly with the aforementioned other effective components or the aforementioned components for drug preparation can be formed into tablets by tablet molding, and besides, into any form of such as solid drugs (e.g. granules, powders, capsules), liquid drugs (e.g. solutions, suspensions, emulsions), and freeze dry drugs.

In the case of the direct injection into diseased parts, a material obtained by diluting the Hyp-Gly with such as physiological saline is used, but, if necessary, the aforementioned other effective components may further be used. Their concentrations are favorably such that as aforementioned, the content of the Hyp-Gly will not be less than 1 mmol/L.

The dipeptide which is contained in the malady inhibitor according to the present invention as an essential effective component is that which has a structure of Hyp-Gly and differs from such as amino acids, dipeptides having a structure other than Hyp-Gly, and tripeptides and more multivalent peptides where another amino acid is bonded to the Hyp-Gly. By making the malady inhibitor contain the aforementioned dipeptide having a structure of Hyp-Gly, excellent malady inhibition effects (effects to inhibit symptoms of such as osteoporosis, osteoarthritis and pressure ulcer) are displayed.

What is mentioned above is specifically proved in performance evaluation tests as described in the below-mentioned working example part.

[Joint Use with Other Dipeptides]

There are cases where the malady inhibition effects of the Hyp-Gly can synergistically be enhanced by jointly using it with other dipeptides.

For example, the malady inhibition effects of the Hyp-Gly can synergistically be enhanced by jointly using it with Pro-Hyp.

Furthermore, for example, the effects on maladies such as osteoarthritis can synergistically be enhanced by joint use with Ala-Hyp.

In order to obtain as the collagen peptide according to the present invention, for example, a collagen peptide comprising both the Hyp-Gly and the Pro-Hyp, basically it is enough that only the kind of the enzyme being used in the secondary enzymatic treatment is changed in the same method as the two-step enzymatic treatment method explained about the Hyp-Gly. As such an enzyme, for example, an enzyme having prolidase activity and hydroxyprolidase activity derived from such as *Aspergillus* can be cited.

In the case where the Hyp-Gly and the Pro-Hyp are jointly used in the malady inhibitor according to the present invention, preferable ranges of the content ratios of both are such that when the total of both is 100 weight %, the Hyp-Gly is in the range of 50 to 90 weight %, and the Pro-Hyp is in the range of 10 to 50 weight %.

In addition, in the case where the Hyp-Gly and another dipeptide are jointly used, the content ratio of the dipeptides to the entirety of the aforementioned malady inhibitor according to the present invention is, for example, such that the total amount of the dipeptides is favorably a ratio of not less than 0.001 weight part and that more favorably, they are contained in a ratio of not less than 0.01 weight part. Furthermore, in the case where the malady inhibitor according to the present invention is used by directly injecting it into a diseased part, the total content of the dipeptides is favorably not less than 10 μmol/L.

The synergistic effects by joint use with other dipeptides are hereinafter specifically explained by citing as examples the above representative symptoms which the malady inhibitor according to the present invention can inhibit, namely, osteoporosis, osteoarthritis and pressure ulcer.

As aforementioned, the osteoporosis is such that the bone absorption is made by osteoclasts, and as differentiation and activation of the osteoclasts become greater, the bone absorption ratio becomes higher, while the bone formation is made by osteoblasts, and as differentiation and activation of the osteoblasts become greater, the bone formation ratio becomes higher. Therefore, the osteoporosis can be inhibited by inhibiting the differentiation and activation of the osteoclasts and promoting the differentiation and activation of the osteoblasts. Then, according to the present inventor's knowledge and findings, the Hyp-Gly and the Pro-Hyp show the following functions in the differentiation and activation of the osteoclasts and osteoblasts.

That is to say, first of all, the mechanisms of the differentiation and activation of the osteoclasts are explained. To begin with, (i) a plurality of precursory osteoclasts fuse together and differentiate into multinucleate giant cells. An enzyme which catalyzes this differentiation is TRAP (Tartaric Acid Resistant Acid Phosphatase). Subsequently, (ii) the aforementioned multinucleate giant cells (osteoclasts) dissolve and decompose bone tissue. In the aforementioned mechanism, the Hyp-Gly mainly inhibits the (i), and the Pro-Hyp inhibits both of the (i) and (ii). Therefore, it is suggested that by jointly using the Hyp-Gly and the Pro-Hyp, these synergistically act to display more excellent effects.

In addition, the osteoblasts synthesize and secrete a bone substrate (I type collagen), and ALP (Alkaline Phosphatase) calcifies this bone substrate into $Ca_{10}(PO_4)_6(OH)_2$ (hydroxyapatite), so that ossification is promoted. Hereupon, the Hyp-Gly promotes the aforementioned ALP activity, and further, by jointly using it with the Pro-Hyp, the promoting effect of the Hyp-Gly is promoted by an synergistic effect, so that a promoting effect which is more excellent than the use of each dipeptide alone can be displayed.

The osteoarthritis is graduated into the following four periods: (i) a cell proliferation period, (ii) a cartilage cell differentiation/maturation period, (iii) a period of differentiation (degeneration) into hypertrophied cartilage cells, (iv) calcification and subsequent apotrosis (programmed death of cells). In the (i) and (ii), mainly the Pro-Hyp contributes to promotion of differentiation into cartilage cells and to its maintenance, and further in the (ii), the Hyp-Gly adjusts differentiation of precursory articular cartilage cells, catalyzes differentiation (degeneration) into hypertrophied cartilage cells, and inhibits activity of ALP (Alkaline Phosphatase) being also a specific marker, so that the transition to the (iii) is inhibited. Hereupon, according to the present inventor's knowledge and findings, if an Ala-Hyp is also jointly used, then the functions of the Hyp-Gly in the (ii), namely, the adjustment of differentiation of precursory articular cartilage cells and the inhibition of activity of ALP, are synergistically enhanced. In this way, it is suggested that by jointly using the Hyp-Gly and the Pro-Hyp and preferably also jointly using the Ala-Hyp, the degeneration of cartilage cells is synergistically inhibited, and the expression type of articular cells is maintained, so that the inhibition of the osteoarthritis is contributed to.

The process of symptoms and healing of the pressure ulcer is graduated into the following three periods: (i) an inflammation reaction period, (ii) a proliferation period (granulating period) and (iii) a stable period.

That is to say, if skin is damaged, then in (i) the inflammation reaction period, rupture of tissue and rupture of blood vessels occur, and hemorrhage occurs locally. However, hemostasis is made by function of such as coagulation factors in blood and by shrinkage of blood vessels. Next, such as lymphocytes and monocytes get out of blood vessels as exudates and move to a wound (cell wandering). Hereupon, the Pro-Hyp displays a function to promote the cell wandering of the lymphocytes and monocytes. The monocytes become macrophages, and they further release various chemical substances and become generation sources of the next signals. In addition, collagen fibers in skin dermis are secreted by endogenous collagenase (e.g. MMP-13).

Next, in (ii) the proliferation period, the chemical substances released by activity of the macrophages and a collagen-decomposed fragment peptide (e.g. Pro-Hyp and Hyp-Gly) formed by the aforementioned endogenous collagenase give stimulations to gather fibroblasts, so that collagen fibers (collagen: mainly comprising tropocollagen) are formed. The fibroblasts, capillary vessels and collagen co-operate, exude to a wound, embed a defective surface, and fuse the wound surface (granulation tissue formation). Hereupon, both of the Pro-Hyp and the Hyp-Gly synergistically promote collagen synthesis to promote the granulation tissue formation. Particularly, at the initial stage of (ii) the proliferation period, mainly the Pro-Hyp displays a physiological function, and at the late stage, mainly the Hyp-Gly displays a physiological function. If granulation tissue is formed, then non-proliferative cells other than a germinal layer move to form one epithelial cell layer. Then, to under this layer, cells of the germinal layer move and proliferate from a wound margin to form a multilayered epidermis, so that epidermis formation is completed.

Finally, in the period (iii), the activity of the fibroblasts reverts to an ordinary one, the formation of collagen decreases, the formation amount and the decomposition amount transit to a stationary state while keeping the balance, so that healing is completed.

The above functions of the dipeptide which is contained in the collagen peptide according to the present invention is suggested also from proof of various effects in performance evaluation tests as described in the below-mentioned working example part.

[Pro-Hyp]

The above Pro-Hyp has the functions to inhibit symptoms of such as osteoporosis, osteoarthritis and pressure ulcer not only in the case where the Pro-Hyp is jointly used with the Hyp-Gly, but also in the case where the Pro-Hyp is used alone.

Hereinafter, this Pro-Hyp is explained in detail. However, since much of its subject matter overlaps with the above explanation about the Hyp-Gly, different points are mainly explained.

In the Pro-Hyp, the proline unit and/or the hydroxyproline unit may be chemically modified. Particularly, as to the hydroxyproline unit, either or both of the carboxyl group and the hydroxyl group may be chemically modified.

Thus, in the present specification, when a "dipeptide having a structure of Pro-Hyp" or its abbreviation "Pro-Hyp" is mentioned, this matter encompasses both a chemically modified one and a non-chemically-modified one.

In the case where the Pro-Hyp is chemically modified, it can be made soluble in the range of weak acidity to neutrality, and such as enhancement of compatibility with other effective components can also be expected. Specifically, as to the α-amino group of the proline residue, chemical modifications such as polypeptidylation, succinylation, maleylation, acetylation, deamination, benzoylation, alkylsulfonylation, arylsulfonylation, dinitrophenylation, trinitrophenylation, carbamylation, phenylcarbamylation, and thiolation can be cited. As to the α-carboxyl group of the hydroxyproline residue, chemical modifications such as esterification and amidation can be cited. As to the hydroxyl group of the hydroxyproline residue, chemical modifications such as O-acetylation can be cited. Proper chemical modifications may be selected according to such as the kinds of other effective components.

The ratio in which the aforementioned Pro-Hyp is contained in the malady inhibitor and further the content of the Pro-Hyp in the case where the malady inhibitor is used by injection into an articular local part may be the same as the ratio and content mentioned for the Hyp-Gly.

Similarly to the Hyp-Gly, the aforementioned Pro-Hyp can, for example, obtained by enzymatically treating collagen or gelatin in two separated steps or being synthesized from amino acids. As to the chemical modification, publicly known means as mentioned below can be cited.

The enzymatic treatment method for obtaining the Pro-Hyp, basically, may be the same method as the two-step enzymatic treatment method explained about the Hyp-Gly. However, for the secondary enzymatic treatment, for example, an enzyme having aminopeptidase P and prolidase activity derived from such as *Aspergillus* is used.

Similarly to the Hyp-Gly, the Pro-Hyp can be synthesized from amino acids. However, in this case, it is enough to simply replace hydroxyproline with proline, and glycine with hydroxyproline, in the above-explained method for synthesizing the Hyp-Gly.

As previously mentioned, the Pro-Hyp may be a chemically modified one. To specific means and treatment conditions of the chemical modification, conventional chemical modification techniques for peptides are applied.

As to chemical modification of the α-amino group of the proline residue, for example, the polypeptidylation can be carried out by a reaction with such as N-carboxylic anhydride, and the succinylation or maleylation can be carried out by a reaction with such as succinic anhydride or maleic anhydride near pH 8, and the acetylation can be carried out by a reaction with such as N-hydroxysuccinimide acetate near neutrality, and the deamination can be carried out by making such as nitrous acid act, and the benzoylation can be carried out by making such as benzoyl chloride or benzoic anhydride act, and the alkylsulfonylation or arylsulfonylation can be carried out by a reaction with such as benzenesulfonyl chloride, p-toluenesulfonyl chloride, or methanesulfonyl chloride, and the dinitrophenylation or trinitrophenylation can be carried out by making such as 2,4-dinitrofluorobenzene or 2,4,6-trinitrobenzenesulfonic acid act, and the carbamylation or phenylcarbamylation can be carried out by making such as cyanic acid act, and the thiolation can be carried out by making such as N-acetylhomocystinethiolactone, S-acetylmercaptosuccinic anhydride, thioparaconic acid, or S-acetylthioitamalic anhydride act.

As to chemical modification of the α-carboxyl group of the hydroxyproline residue, for example, the esterification can be carried out by passing a dry hydrogen chloride gas after suspending into methanol, and the amidation can be carried out by making such as carbodiimide act.

As to chemical modification of the hydroxyl group of the hydroxyproline residue, for example, the O-acetylation can be carried out by making anhydrous acetic acid act in water solvent or in a non-water solvent.

As other specific examples of the chemical modification, chemical modification techniques as disclosed in such as JP-B-62-044522 and JP-B-05-079046 can be applied.

As to details of the malady inhibitor comprising the Pro-Hyp as an effective component, since they are common to those which are aforementioned about the malady inhibitor comprising the Hyp-Gly as an effective component, their explanation is omitted.

[Ala-Hyp]

The above Ala-Hyp has the functions to inhibit symptoms of such as osteoarthritis not only in the case where the Ala-Hyp is jointly used with the Hyp-Gly, but also in the case where the Ala-Hyp is used alone.

Hereinafter, this Ala-Hyp is explained in detail. However, since much of its subject matter overlaps with the above explanations about the Hyp-Gly and the Pro-Gly, different points are mainly explained.

In the Ala-Hyp, the alanine unit and/or the hydroxyproline unit may be chemically modified. Particularly, as to the hydroxyproline unit, either or both of the carboxyl group and the hydroxyl group may be chemically modified.

Thus, in the present specification, when a "dipeptide having a structure of Ala-Hyp" or its abbreviation "Ala-Hyp" is mentioned, this matter encompasses both a chemically modified one and a non-chemically-modified one.

In the case where the Ala-Hyp is chemically modified, it can be made soluble in the range of weak acidity to neutrality, and such as enhancement of compatibility with other effective components can also be expected. Basically, the same chemical modifications as those aforementioned about the Pro-Hyp can be made. Specifically, as to the α-amino group of the alanine residue, the same chemical modifications as those aforementioned about the α-amino group of the proline residue in the Pro-Hyp can be made. As to the α-amino group and hydroxyl group of the hydroxyproline residue, the same chemical modifications as those aforementioned about the α-amino group and hydroxyl group of the hydroxyproline residue in the Pro-Hyp can be made. Proper chemical modifications may be selected according to such as the kinds of other effective components.

The ratio in which the aforementioned Ala-Hyp is contained in the malady inhibitor and further the content of the Ala-Hyp in the case where the malady inhibitor is used by injection into an articular local part may be the same as the ratio and content mentioned for the Hyp-Gly.

Similarly to the Hyp-Gly, the aforementioned Ala-Hyp can, for example, obtained by enzymatically treating collagen or gelatin in two separated steps or being synthesized from amino acids. As to the chemical modification, publicly known means as mentioned below can be cited.

The enzymatic treatment method for obtaining the Ala-Hyp, basically, may be the same method as the two-step enzymatic treatment method explained about the Hyp-Gly. However, for the secondary enzymatic treatment, for example, an enzyme having proteinase activity and hydroxyprolirase activity derived from such as *Aspergillus* is used.

Similarly to the Hyp-Gly, the Ala-Hyp can be synthesized from amino acids. However, in this case, it is enough to simply replace hydroxyproline with alanine, and glycine with hydroxyproline, in the above-explained method for synthesizing the Hyp-Gly.

As previously mentioned, the Ala-Hyp may be a chemically modified one. To specific means and treatment conditions of the chemical modification, conventional chemical modification techniques for peptides are applied. As to the α-amino group of the alanine residue, the same chemical modifications as those aforementioned about the α-amino group of the proline residue in the Pro-Hyp may be made. As to the α-amino group and hydroxyl group of the hydroxyproline residue, the same chemical modifications as those aforementioned about the α-amino group and hydroxyl group of the hydroxyproline residue in the Pro-Hyp may be made.

As to details of the malady inhibitor comprising the Ala-Hyp as an effective component, since they are common to those which are aforementioned about the malady inhibitor comprising the Hyp-Gly as an effective component, their explanation is omitted.

WORKING EXAMPLES

Hereinafter, the present invention is more specifically illustrated by performance evaluation tests of the dipeptide according to the present invention or the collagen peptide comprising this dipeptide and by examples of compositions of malady inhibitors comprising the aforementioned dipeptide as an effective component. However, the present invention is not limited to them. Hereinafter, for convenience, the unit "parts by weight" may be simply referred to as "parts" and the unit "% by weight" may be simply referred to as "%".

[Dipeptides]

Example 1

An Hyp-Gly was synthesized by the aforementioned solid-phase method.

That is to say, beads of a polystyrene polymer gel of about 0.1 mm in diameter of which the surface was modified with an amino group were used as a solid phase, and 45 parts of glycine was bonded (peptide-bonded) to 45 parts of hydroxyproline (of which the amino group was protected by the Fmoc (fluorenyl-methoxy-carbonyl) group) by a dehydration reaction using 10 parts of diisopropylcarbodiimide (DIC) as a condensing agent, and then the solid phase was well washed with a solvent (ethyl alcohol) to remove such as residual glycine. Thereafter, the protecting group of the hydroxyproline residue which was bonded to the solid phase was removed (deprotected) by maceration of trifluoroacetic acid, so that an Hyp-Gly was synthesized.

For this dipeptide synthesis, a Liberty peptide synthesis system (produced by CEM) was used.

Example 2

A mixture of the Hyp-Gly of Example 1 and the below-mentioned Pro-Hyp of Referential Example 1-1 in a ratio of 1:1 (based on weight) was taken as Example 2.

Example 3

A mixture of the Hyp-Gly of Example 1, the below-mentioned Pro-Hyp of Referential Example 1-1 and the below-mentioned Ala-Hyp of Referential Example 1-2 in a ratio of 1:1:1 (based on weight) was taken as Example 3.

Referential Example 1-1

A Pro-Hyp was synthesized in the same way as of the above synthesis method of the Hyp-Gly except that the hydroxyproline was replaced with proline, and the glycine was replaced with hydroxyproline. The resultant Pro-Hyp was taken as Referential Example 1-1.

Referential Example 1-2

An Ala-Hyp was synthesized in the same way as of the above synthesis method of the Hyp-Gly except that the hydroxyproline was replaced with alanine, and the glycine was replaced with hydroxyproline. The resultant Ala-Hyp was taken as Referential Example 1-2.

Comparative Example 1

A Leu-Hyp was synthesized in the same way as of the above synthesis method of the Hyp-Gly except that the hydroxyproline was replaced with leucine, and the glycine was replaced with hydroxyproline. The resultant Leu-Hyp was taken as Comparative Example 1.

Comparative Example 2

A Phe-Hyp was synthesized in the same way as of the above synthesis method of the Hyp-Gly except that the hydroxyproline was replaced with phenylalanine, and the glycine was replaced with hydroxyproline. The resultant Phe-Hyp was taken as Comparative Example 2.

Comparative Example 3

An Ser-Hyp was synthesized in the same way as of the above synthesis method of the Hyp-Gly except that the hydroxyproline was replaced with serine, and the glycine was replaced with hydroxyproline. The resultant Ser-Hyp was taken as Comparative Example 3.

[Tripeptide]

Comparative Example 4

A Pro-Hyp-Gly was synthesized in the same way as of the above synthesis method of the Hyp-Gly except that the hydroxyproline was replaced with proline, and the glycine was replaced with the Hyp-Gly synthesized in Example 1. The resultant Pro-Hyp-Gly was taken as Comparative Example 4.

[Amino Acids]

Comparative Examples 5 and 6

Proline being an amino acid was taken as Comparative Example 5, and hydroxyproline was taken as Comparative Example 6.

[Collagen Peptides]

Example 4

A pig skin-derived collagen peptide (PC) containing an Hyp-Gly was obtained by the following method and taken as Example 4.

An amount of 1 kg of gelatin (I type collagen) being a heat-degenerated product of a pig skin-derived collagen was dissolved into 4 L of 75° C. warm water, and its temperature was adjusted to 60° C., and thereafter as a primary reaction, 10 g of yellow *Aspergillus*-derived protease was added, and the system was kept at a pH of 5.0 to 6.0 and a temperature of 45 to 55° C. for 120 minutes, thereby carrying out an enzymatic hydrolysis treatment. Next, as a secondary enzymatic reaction, an *Aspergillus oryzae*-extracted enzyme having hydroxyprolidase activity was added so as to be 1.5% in end concentration, so that the material was made soluble. Thereafter, the material was reacted at 50° C. for 6 hours. After the reaction, the reaction liquid was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a pig skin-derived collagen peptide (PC) was obtained.

This PC was subjected to thin-layer chromatography (TLC). That is to say, 10 μg of the water-solubilized PC was dropped (spot origin) onto a TLC plate (trade name: "Cellulose F", produced by Merck) and dried and then eluted with a solvent (n-butanol:acetic acid:water=4:1:2). This plate was air-dried and then sprayed with an isatin-zinc acetate color former (prepared by dissolving 1 g of isatin and 1.5 g of zinc acetate into 100 mL of isopropanol under heating and, after cooling, adding 1 mL of acetic acid), thereby confirming that the Rf value {[distance from spot original to colored spot]/ [distance from spot original to solvent-eluted front]} of the blue spot of the above-obtained PC consisted with the Rf value of the blue spot of the Hyp-Gly among the Hyp-Gly and the Pro-Hyp which were internal markers spotted to the same plate, in other words, this PC contained the Hyp-Gly.

Incidentally, the sum (Y) of sequences of the Hyp-Gly being contained in a pig skin-derived I type collagen (weight (X) g) of which the amino acid sequence was already known was counted, and the theoretical content of the Hyp-Gly in the entirety of the I type collagen was determined from the following formula, so that it was 20.0 weight %.

((Number(Y) of Hyp-Gly)×(weight(molecular weight) of Hyp-Gly))/(weight(X) of all sequences)

From the above, it follows that the aforementioned PC contains the Hyp-Gly theoretically in a ratio of 20.0 weight % at the maximum.

Example 5

A fish scale-derived collagen peptide (FC) containing an Hyp-Gly was obtained in the same way as of the aforementioned production of the PC except that a fish scale-derived gelatin was used. It was taken as Example 5.

This FC was analyzed by TLC in the same way as of the aforementioned case of the PC. As a result, the presence of an Hyp-Gly was confirmed.

Incidentally, the sum (Y) of sequences of the Hyp-Gly being contained in a fish scale-derived I type collagen (weight (X) g) of which the amino acid sequence was already known was counted, and the theoretical content of the Hyp-Gly in the entirety of the I type collagen was determined from the following formula, so that it was 23.5 weight %.

((Number(Y) of Hyp-Gly)×(weight(molecular weight) of Hyp-Gly))/(weight(X) of all sequences)

From the above, it follows that the aforementioned FC contains the Hyp-Gly theoretically in a ratio of 23.5 weight % at the maximum.

Example 6

A pig skin-derived collagen peptide (PC-CP) containing an Hyp-Gly was obtained by the following method and taken as Example 6.

An amount of 1 kg of gelatin (I type collagen) being a heat-degenerated product of a pig skin-derived collagen was dissolved into 4 L of 20 mM Tris-HCl buffer (pH 7.5) while heated and then cooled to 40° C., and thereafter as a primary enzymatic reaction, 1 g of collagenase (Collagenase N2, produced by Nitta Gelatin, Inc.) was added, and the system was kept at a pH of 7.0 to 7.8 and a temperature of 40° C. for 24 hours, thereby carrying out an enzymatic decomposition treatment. Next, as a secondary enzymatic reaction, an *Aspergillus niger*-extracted enzyme having hydroxyprolidase activity was added to the resultant reaction liquid so as to be 1.0% in end concentration, so that the material was made soluble. Thereafter, the material was reacted at pH 4.0 and 50° C. for 6 hours. After the reaction, the reaction liquid was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC-CP was obtained.

In addition, this PC-CP was analyzed by TLC in the same way as of the aforementioned case of the PC. As a result, the presence of an Hyp-Gly was confirmed.

Incidentally, the sum (Y) of sequences of the Hyp-Gly being contained in a pig skin-derived I type collagen (weight (X) g) of which the amino acid sequence was already known was counted, and the theoretical content of the Hyp-Gly in the entirety of the I type collagen was determined from the following formula, so that it was 20.0 weight %.

((Number(Y) of Hyp-Gly)×(weight(molecular weight) of Hyp-Gly))/(weight(X) of all sequences)

From the above, it follows that the aforementioned PC-CP contains the Hyp-Gly theoretically in a ratio of 20.0 weight % at the maximum.

Example 7

A pig skin-derived collagen peptide (PC-PH) containing an Hyp-Gly and a Pro-Hyp was obtained by the following method and taken as Example 7.

An amount of 1 kg of gelatin (I type collagen) being a heat-degenerated product of a pig skin-derived collagen was dissolved into 4 L of 75° C. warm water, and its temperature was adjusted to 60° C., and thereafter as a primary enzymatic reaction, 10 g of yellow *Aspergillus*-derived protease was added, and the system was kept at a pH of 5.0 to 6.0 and a temperature of 45 to 55° C. for 120 minutes, thereby carrying out an enzymatic hydrolysis treatment. Next, as a secondary enzymatic reaction, an *Aspergillus niger*-extracted enzyme having prolidase activity and hydroxyprolidase activity was added so as to be 1.5% in end concentration, so that the material was made soluble. Thereafter, the material was reacted at a pH of 4.5 to 5.5 and a temperature of 45 to 50° C. for 6 hours. After the reaction, the reaction liquid was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC-PH was obtained.

In addition, this PC-PH was analyzed by TLC in the same way as of the aforementioned case of the PC. As a result, the Rf value of the blue spot of the PC-PH consisted with the Rf value of the blue spot of each of the Hyp-Gly and the Pro-Hyp, so that it was confirmed that the PC-PH contained both of the Hyp-Gly and the Pro-Hyp.

Comparative Example 7

A collagen peptide (PC-CP-Cont) containing neither Hyp-Gly nor Pro-Hyp was obtained by carrying out only the primary enzymatic reaction in the aforementioned production of the PC-CP and taken as Comparative Example 7.

That is to say, 1 kg of gelatin (I type collagen) being a heat-degenerated product of a pig skin-derived collagen was dissolved into 4 L of 20 mM Tris-HCl buffer (pH 7.5) while heated and then cooled to 40° C., and thereafter as a primary enzymatic reaction, 1 g of collagenase (Collagenase N2, produced by Nitta Gelatin, Inc.) was added, and the system was kept at a pH of 7.0 to 7.8 and a temperature of 40° C. for 24 hours, thereby carrying out an enzymatic decomposition treatment. Next, a solution obtained by the enzymatic hydrolysis treatment was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC-CP-Cont was obtained.

In addition, this PC-CP-Cont was analyzed by TLC in the same way as of the aforementioned case of the PC. As a result, the presence of any of the Hyp-Gly and the Pro-Hyp could not be confirmed.

[Performance Evaluation Tests]

Details of performance evaluation tests for the above dipeptides, tripeptide, amino acids and collagen peptides of Examples 1 to 7, Referential Examples 1-1 and 1-2 and Comparative Examples 1 to 7 are shown below.

<Evaluation Test 1-1: Inhibition of Differentiation and Activation of Osteoclasts>

The evaluation was carried out in accordance with Kobayashi Y. et al.'s osteoclast differentiation culture method [J. Bone Miner. Metab. (2004) 22: p. 318-328].

That is to say, the Hyp-Gly and a 1:1 mixture of the Hyp-Gly and the Pro-Hyp were used, and each of them was added to a primary mouse bone marrow cell culture liquid so as to be 625 μM in end concentration. After 6 days from the culture, each inhibition activity of tartaric acid resistant acid phosphatase (TRAP) being a marker enzyme was examined. In the same way, the TRAP inhibition activity when using the other dipeptides (Pro-Hyp, Ala-Hyp, Leu-Hyp, Phe-Hyp, Ser-Hyp), the tripeptide (Pro-Hyp-Gly) and the amino acids (Pro, Hyp) was examined. Furthermore, as a control, the TRAP inhibition activity when adding no peptide (blank) was also examined.

In addition, the degree of inhibition of differentiation and activation of osteoclasts by the various peptides and amino acids was evaluated by the following Pit assay. That is to say, the Pit assay where osteoclasts were cultured on odontoblast pieces was carried out in accordance with Kakudo S, et al. (1996). J. Bone Miner. Metab. 14: 129-136, specifically, as follows.

Precursory cells of osteoclasts derived from young mouse intestinal bone were freeze-preserved at −80° C. together with a bone marrow stroma cells-containing suspension in the presence of 10% DMSO, thereby making matured osteoclasts extinct.

These cells of $2.0 \times 10^5$ in number were seeded into each well of a 96-well plate where dentin slices were set, and each peptide to be tested was added to the culture liquid, and culture was carried out at 37° C. in 5% $CO_2$ for about 1 week. Thereafter, cells were removed from the dentin slices by a silicon-made rubber POLICEMAN, and then the dentin slices were dyed with an acid hematoxylin solution for several minutes. Hereupon, the number of TRAP dyeing positive multinucleate giant cells (osteoclasts) was counted by the TRAP dyeing, and the number relative to the number of cells in the control (blank) was calculated. Thereafter, the Pit number (number of absorption pits) by osteoclasts was counted under a microscope, and the degree of inhibition of activity of osteoclasts by each peptide to be tested was indicated by the ratio relative to the blank (control).

The results are shown in Table 1.

<Evaluation Test 1-2: Promotion of Differentiation and Activation of Osteoblasts>

Each of dexamethasone (end concentration: 1 nmol/L), β-glycerophosphoric acid (end concentration: 5 mmol/L), and ascorbic acid (end concentration: 100 μg/mL) was added to an osteoblast stock MC3T3-E1 culture liquid, and then the Hyp-Gly and a 1:1 mixture of the Hyp-Gly and the Pro-Hyp were used, and each of them was added to the aforementioned culture liquid so as to be 2.5 mmol/L in end concentration. After 10 days from the culture, each promotion activity of alkaline phosphatase (ALP) being a marker enzyme for differentiation and calcification of osteoblasts was examined. In the same way, the ALP promotion activity when using the other dipeptides (Pro-Hyp, Ala-Hyp, Leu-Hyp, Phe-Hyp, Ser-Hyp), the tripeptide (Pro-Hyp-Gly) and the amino acids (Pro, Hyp) was examined. Furthermore, as a control, the ALP promotion activity when adding no peptide (blank) was also examined. The results are shown in Table 2.

TABLE 2

|  |  | Relative value (%) of ALP |
|---|---|---|
|  | Control (blank) | 100 |
| Example 1 | Hyp-Gly | 140 ± 24** |
| Example 2 | (Hyp-Gly) + (Pro-Hyp) | 151 ± 17** |
| Referential Example 1-1 | Pro-Hyp | 115 ± 25 |
| Referential Example 1-2 | Ala-Hyp | 112 ± 31 |
| Comparative Example 1 | Leu-Hyp | 92 ± 12 |
| Comparative Example 2 | Phe-Hyp | 109 ± 11 |

TABLE 1

|  |  | Relative number (%) of TRAP positive multinucleate giant cells (osteoclasts) in culture on plastic Petri dish | Relative area (%) of TRAP positive multinucleate giant cells (osteoclasts) in culture on plastic Petri dish | Relative number (%) of TRAP positive multinucleate giant cells (osteoclasts) in culture on dentin slices | Relative number (%) of Pit |
|---|---|---|---|---|---|
|  | Control (blank) | 100 | 100 | 100 | 100 |
| Example 1 | Hyp-Gly | 9 ± 2** | 7 ± 1** | 9 ± 5** | 2 ± 2** |
| Example 2 | (Hyp-Gly) + (Pro-Hyp) | 11 ± 1** | 8 ± 3** | 3 ± 3** | 0** |
| Referential Example 1-1 | Pro-Hyp | 130 ± 9* | 120 ± 12* | 17 ± 6** | 9 ± 2** |
| Referential Example 1-2 | Ala-Hyp | 102 ± 4 | 110 ± 31 | 89 ± 13 | 101 ± 12 |
| Comparative Example 1 | Leu-Hyp | 88 ± 22 | 83 ± 27 | 101 ± 12 | 91 ± 11 |
| Comparative Example 2 | Phe-Hyp | 119 ± 16 | 118 ± 21 | 98 ± 11 | 109 ± 15 |
| Comparative Example 3 | Ser-Hyp | 96 ± 5 | 91 ± 10 | 105 ± 4 | 98 ± 12 |
| Comparative Example 4 | Pro-Hyp-Gly | 109 ± 15 | 113 ± 11 | 91 ± 11 | 97 ± 13 |
| Comparative Example 5 | Pro | 119 ± 44 | 125 ± 69 | 119 ± 20 | 121 ± 23 |
| Comparative Example 6 | Hyp | 126 ± 4* | 117 ± 13* | 141 ± 9* | 131 ± 11* |

Number of tests: n = 6
Note)
**There is statistically a significant difference in comparison with the control. ($p < 0.01$)
*There is statistically a significant difference in comparison with the control. ($p < 0.05$)

TABLE 2-continued

|  |  | Relative value (%) of ALP |
| --- | --- | --- |
| Comparative Example 3 | Ser-Hyp | 91 ± 21 |
| Comparative Example 4 | Pro-Hyp-Gly | 103 ± 22 |
| Comparative Example 5 | Pro | 97 ± 15 |
| Comparative Example 6 | Hyp | 103 ± 25 |

Number of tests: n = 6
Note)
**There is statistically a significant difference in comparison with the control. (p < 0.01)

<Evaluation Test 1-3: Inhibition of Degeneration of Cartilage Cells>

The Hyp-Gly, a 1:1 mixture of the Hyp-Gly and the Pro-Hyp and a 1:1:1 mixture of the Hyp-Gly, the Pro-Hyp and the Ala-Hyp were used, and each dipeptide was added to a precursory cartilage cell stock ATDC5 culture liquid so as to be 2.5 mmol/L in end concentration. After 5 days from the culture, each inhibition activity of alkaline phosphatase (ALP) being a marker enzyme for hypertrophied cartilages and calcification was examined. In the same way, the ALP activity when using the other dipeptides (Pro-Hyp, Ala-Hyp, Leu-Hyp, Phe-Hyp, Ser-Hyp), the tripeptide (Pro-Hyp-Gly) and the amino acids (Pro, Hyp) was examined. Furthermore, as a control, the ALP activity when adding no peptide (blank) was also examined. The results are shown in Table 3.

TABLE 3

|  |  | Relative value (%) of ALP |
| --- | --- | --- |
|  | Control (blank) | 100 |
| Example 1 | Hyp-Gly | 76 ± 21* |
| Example 2 | (Hyp-Gly) + (Pro-Hyp) | 9 ± 3** |
| Example 3 | (Hyp-Gly) + (Pro-Hyp) + (Ala-Hyp) | 7 ± 2** |
| Referential Example 1-1 | Pro-Hyp | 12 ± 2** |
| Referential Example 1-2 | Ala-Hyp | 17 ± 6** |
| Comparative Example 1 | Leu-Hyp | 93 ± 12 |
| Comparative Example 2 | Phe-Hyp | 109 ± 11 |
| Comparative Example 3 | Ser-Hyp | 91 ± 21 |
| Comparative Example 4 | Pro-Hyp-Gly | 84 ± 14 |
| Comparative Example 5 | Pro | 98 ± 10 |
| Comparative Example 6 | Hyp | 101 ± 1 |

Number of tests: n = 6
Note)
**There is statistically a significant difference in comparison with the control. (p < 0.01)
*There is statistically a significant difference in comparison with the control. (p < 0.05)

<Evaluation Test 1-4: Recovery of Tropocollagen Amount in Skin Dermis>

Wister strain male rats (140 g) were preliminarily fed with a commercially available solid food (Type MF, produced by ORIENTAL YEAST Co., Ltd.) for 3 days, and then the feeding was replaced with casein feeding to cause a skin wound after 3 days.

The aforementioned skin wound was caused by applying a fur-removing treatment to an abdominal part of each rat for 3 days. Specifically, Nembutal (4 mg/0.08 mL/100 g BW) was injected into an abdominal cavity of each rat to anesthetize it, and then fur cutting with hair clippers was applied to the abdominal part (about 3×5 cm). Furthermore, thereto a commercially available fur-removing agent (Epilat fur-removing cream, produced by Kanebo Co.) was applied, and then the abdominal part was left for 5 minutes and then shaved with a shaver carefully. This treatment was carried out once a day continuously for 3 days since 3 days before the beginning of sampling of a skin sample.

A test group was classified into a casein-fed group, an Hyp-Gly group, a (Hyp-Gly)+(Pro-Hyp) group (1:1 mixture of Hyp-Gly and Pro-Hyp), a PC group, an FC group, a PC-CP group, and a PC-PH group, and every group was measured by a change of the skin collagen amount (ratio to total collagen amount) in a skin wound recovery process on the day of the fur-removing treatment (0 day after the fur-removing treatment), after 1 day from the fur-removing treatment, after 2 days from the fur-removing treatment and after 4 days from the fur-removing treatment.

The feed compositions for the groups are shown in Table 4.

TABLE 4

| Ingredients | Control (casein feeding) | Hyp-Gly | (Hyp-Gly) + (Pro-Hyp) | PC | FC | PC-CP | PC-PH |
| --- | --- | --- | --- | --- | --- | --- | --- |
| Casein | 150 | 145 | 145 | 100 | 100 | 100 | 101 |
| Hyp-Gly | — | 5 | 2.5 | — | — | — | — |
| Pro-Hyp | — | — | 2.5 | — | — | — | — |
| Collagen peptide | — | — | — | 50 | 50 | 50 | 50 |
| α-Corn starch | 735 | 735 | 735 | 735 | 735 | 735 | 735 |
| Corn oil | 50 | 50 | 50 | 50 | 50 | 50 | 50 |
| Cellulose | 20 | 20 | 20 | 20 | 20 | 20 | 20 |
| Mineral mixture | 35 | 35 | 35 | 35 | 35 | 35 | 35 |
| Vitamin mixture | 10 | 10 | 10 | 10 | 10 | 10 | 10 |
| Total | 1000 | 1000 | 1000 | 1000 | 1000 | 1000 | 1000 |

The rats were fed with the above feed compositions, and the feeds and water were freely ingested during the feeding period.

Furthermore, as to the Hyp-Gly group, the (Hyp-Gly)+(Pro-Hyp) group (1:1 mixture of Hyp-Gly and Pro-Hyp), the PC group, the FC group, the PC-CP group, and the PC-PH group, 10 g of the same as each of the Hyp-Gly, PC, FC, PC-CP, and PC-PH contained in the feeds was precisely weighed out and then dissolved and heat-retained with 20 mL of distilled water and injected into a stomach of the rat of each test group with a sound once a day, at noon.

The results of the measurement of the change of the skin collagen amount (ratio to total collagen amount) in the skin wound recovery process with respect to each group are shown in Table 5.

TABLE 5

Change of skin collagen amount (ratio to total collagen amount) (%) in skin wound recovery process

|  | No treatment | 0 day after fur-removing treatment | 1st day after fur-removing treatment | 2nd day after fur-removing treatment | 4th day after fur-removing treatment |
|---|---|---|---|---|---|
| Control (casein feeding) | $8.2 \pm 0.6^a$ | $2.9 \pm 0.3^b$ | $2.5 \pm 0.2^b$ | $2.6 \pm 0.3^b$ | $3.1 \pm 0.4^b$ |
| Example 1 Hyp-Gly | $8.2 \pm 0.6^a$ | $2.4 \pm 0.2^b$ | $3.1 \pm 0.3^{c\ b}$ | $4.0 \pm 0.2^c$ | $5.2 \pm 0.3^d$ |
| Example 2 (Hyp-Gly) + (Pro-Hyp) | $8.2 \pm 0.6^a$ | $2.3 \pm 0.1^b$ | $3.2 \pm 0.2^c$ | $4.3 \pm 0.3^c$ | $7.3 \pm 0.7^a$ |
| Example 4 PC | $8.2 \pm 0.6^a$ | $2.1 \pm 0.3^b$ | $2.3 \pm 0.1^{c\ b}$ | $3.1 \pm 0.3^c$ | $4.6 \pm 0.2^d$ |
| Example 5 FC | $8.2 \pm 0.6^a$ | $2.6 \pm 0.3^b$ | $2.5 \pm 0.3^b$ | $3.5 \pm 0.2^c$ | $4.5 \pm 0.4^d$ |
| Example 6 PC-CP | $8.2 \pm 0.6^a$ | $2.5 \pm 0.1^b$ | $3.1 \pm 0.4^{c\ b}$ | $3.8 \pm 0.1^c$ | $5.1 \pm 0.2^d$ |
| Example 7 PC-PH | $8.2 \pm 0.6^a$ | $2.3 \pm 0.2^b$ | $3.2 \pm 0.2^c$ | $4.1 \pm 0.4^c$ | $7.1 \pm 0.8^a$ |

Number of tested animals: n = 4
Note)
There is statistically a significant difference between different alphabets. (p < 0.05)
(Note):
skin tropocollagen ratio (%) = ①  ÷ [① + ② + ③] × 100
①: 0.45M aqueous NaCl solution soluble collagen amount: tropocollagen amount
②: 0.5M aqueous acetic acid solution soluble collagen amount: acid soluble collagen amount
③: 0.5M aqueous acetic acid solution insoluble collagen amount: (acid insoluble collagen = crosslinked collagen) amount Hereupon, the quantification of the soluble skin collagen was carried out as follows.

While fats under skin were removed as much as possible, treated skin and untreated skin were trimmed. They were carefully cut into thin pieces with scissors for dissection, and about 0.2 to about 0.3 g of them were precisely weighed out and taken into a centrifugal sedimentation tube having a capacity of 14 mL. Thereto 4 mL of cold 0.45 M sodium chloride solution was added, and homogenization was carried out with a POLYTRON homogenizer (speed No. 4) for 20 seconds while icing. Furthermore, 2 mL of cold 0.45 M sodium chloride solution was added, and extraction was carried out with a rotating stirrer (produced by TAITEC) in a refrigeration room for 24 hours. An amount of 20,000 g of the resultant extract was centrifuged with a cooling centrifuge for 20 minutes, and the resultant supernatant was taken and designated as a neutral salt soluble collagen fraction. To the centrifugal residue, 6 mL of cold 0.5 M acetic acid was added, and extraction was carried out in the same way for 24 hours. An amount of 20,000 g of the resultant extract by the 0.5 M acetic acid was centrifuged with a cooling centrifuge for 20 minutes, and the resultant supernatant was taken and designated as an acid soluble collagen fraction. The centrifugal residue was designated as an insoluble collagen fraction.

To 5 mL of each of the neutral salt soluble collagen fraction and the acid soluble collagen fraction, there was added the same volume of 5 mL of concentrated hydrochloric acid, and to the insoluble collagen fraction, there was added 1 mL of concentrated hydrochloric acid, and these fractions were dissolved by heating at 60° C. for 5 minutes and then transferred into a glass test tube for hydrolysis while thrice washed with 2 mL of 6 N hydrochloric acid, and hydrolyzed at 110° C. for 24 hours.

Then, the amount of hydroxyproline contained in a hydrolyzed liquid of each collagen fraction was colorimetrically quantified, whereby each collagen fraction was quantified, and the relative ratio of the aforementioned neutral salt soluble collagen fraction to the total of the collagen fractions was calculated.

The above colorimetric quantification of the amount of hydroxyproline was carried out by the Firschein and Shill method, specifically, as follows.

An amount of 2 mL of 2-propanol was added to 2 mL of sample solution, and stirring was carried out enough. Thereto 0.5 mL of chloramine T liquid being an oxidant was added, and the mixture was left for precisely 4 minutes and then iced. Thereto 5 mL of p-dimethylaminobenzaldehyde solution was added, and the mixture was stirred enough and then heated in a boiled water bath for precisely 2 minutes and immediately thereafter iced and then left for 1 hour and then subjected to colorimetric quantification at a wavelength of 575 nm.

Incidentally, the chloramine T liquid was prepared by dissolving chloramine T (5 g) into 50 mL of distilled water and then preserved under refrigeration in advance and then, just before the use, diluted with an acetic acid buffer (pH 6.0) into a ratio of 1:4 and then used. In addition, the p-dimethylaminobenzaldehyde solution (Ehrlich solution) was prepared by adding 22 mL of concentrated hydrochloric acid to 20 g of p-dimethylaminobenzaldehyde powder and dissolving it by heating in boiled water and immediately thereafter cooling the resultant solution in ice water and adding thereto 122 mL of 2-propanol and carrying out dissolution by stirring.

<Evaluation Test 1-5: Intestine Absorbency>

Wister strain male rats (170 g) were caused to go on a fast of one night and then subjected to experiments. Each of Hyp-Gly, Pro-Hyp, Ala-Hyp and Ser Hyp was used in an amount of 215 nmol/10 mL for a test sample and injected into stomachs.

As a test method, a cannula was equipped to a heart and portal vein of each rat, and one-directional perfusion was carried out. The perfusion liquid being used was prepared in a way that to a Krebs-Ringer bicarbonate solution (KRB solution, pH 7.4) comprising 9.0 g of NaCl, 8 mL of 5.75% KCl, 2 mL of 10.55% $KH_2PO_4$, 2 mL of 19% $MgSO_4$, 2.73 g of $NaHCO_3$, 3.43 g of glucose and 1255 mL of water, there was added 10 g of bovine serum albumin, 0.5 mL of dexamethasone (0.123 mg/mL) and 0.5 mL of noradrenaline (0.024 mg/mL) relative to 500 mL of the aforementioned KRB solution.

An amount of 0.5 mL of 30% sulfosalicylic acid was added to 5.0 mL of perfusion sample liquid taken from portal vein, and the resultant mixture was vigorously stirred and then left in a refrigerator for one night. This sample was centrifuged at 3000 rpm for 10 minutes to remove protein. As to the resultant centrifugal supernatant, the amount of hydroxyproline in 0.5 mL thereof was colorimetrically quantified, thereby obtaining a free type Hyp amount.

Furthermore, 3.0 mL of the aforementioned centrifugal supernatant was weighed out and placed into a screw opening test tube, and thereto an equivalent of concentrated hydrochloric acid was added to carry out hydrolysis at 110° C. for 24 hours. Concentration to dryness was carried out with an evaporator to remove hydrochloric acid, and then the residue was dissolved into 5 mL of distilled water, and thereto several drops of saturated lithium hydroxide solution were added to adjust pH to the range of 5 to 7, and the volume was adjusted to 10 mL. As to 2 mL of the resultant solution, the amount of hydroxyproline was colorimetrically quantified, thereby obtaining a total Hyp amount. A value obtained by subtracting the free type Hyp amount before hydrolysis from the total Hyp amount after hydrolysis is a peptide-form Hyp amount. From this peptide-form Hyp amount, first of all, the quantified value of each dipeptide (of each test sample) absorbed into the rat portal vein perfusion liquid was confirmed.

In the above, the colorimetric quantification of the amount of hydroxyproline was carried out by the Firschein and Shill method as specifically explained for evaluation test 1-4.

Furthermore, the identification and quantification of the dipeptides as recovered into the rat portal vein perfusion liquid, namely, Hyp-Gly, Pro-Hyp, Ala-Hyp and Ser-Hyp as absorbed into intestine, were carried out by the following HPLC analysis and mass analysis (LC/MS/MS).

(HPLC Analysis)

Analysis of the dipeptides in the perfusion liquid was carried out by reversed-phase HPLC analysis. As HPLC apparatus, LCSS-905 system produced by JASCO Corporation comprising a liquid-feeding pump, a decassa, an autosamplor, a column oven, ultraviolet spectrophotometer, a printer and a system controller was used. As the reversed-phase column, Nova Pak C18 (3.9×150 mm) was used.

A linear-gradient moving bed of a 0.1% TFA-containing acetonitrile-water system was used, the injection amount of the sample was 70 µL, and the flow rate was 1 mL/min.

(LC/MS/MS Analysis)

As HPLC apparatus, U980HPLC (produced by JASCO Corporation) was used. This apparatus was equipped with an ODS (C18) column (Mightysil RP-18, 2×250 mm, produced by Kanto Chemical Co Ltd). The moving bed solvent was a 0.2% formic acid-containing acetonitrile-water system, and the concentration was raised from 0% to 40% acetonitrile by linear gradient in 40 minutes, and washing was carried out with 100% acetonitrile for 10 minutes. The injection amount of the sample was 10 µL, and the column temperature was 40° C.

The MS analysis was carried out in accordance with an MS/MS system with a Quattro LC mass spectrophotometer (Micromass, Manchester, UK) by a Multiple Reaction Monitoring method of 4 channels. That is to say, an eluate from the HPLC was monitored by m/z being $[M+H]^+$ and m/s of its fragment ion species. The Pro-Hyp was monitored by using $[M+H]^+$ m/z: 229.1>132.1, the Ser-Hyp was monitored by using $[M+H]^+$ m/z: 219.1>132.1, the Ala-Hyp was monitored by using $[M+H]^+$ m/z: 203.1>132.1, and the Hyp-Gly was monitored by using $[M+H]^+$ m/z: 189.1>86.1.

The perfusion liquid was treated with sulfosalicylic acid of 3% in end concentration to remove protein. The supernatant was freeze-dried, and 10 mg of the resultant dried powder was dissolved into distilled water and treated with a cation-exchange resin column, thereby obtaining an ammonia-eluted fraction. The solvent was removed from this fraction, and the residue was dissolved into distilled water, and the resultant solution was subjected to LC/MS/MS analysis.

The results were as shown in Table 6.

TABLE 6

| Dosed dipeptide | | Amount (n mol/mL) of each dipeptide identified after absorption |
|---|---|---|
| Example 1 | Hyp-Gly | 9.8 |
| Referential Example 1-1 | Pro-Hyp | 21.3 |
| Referential Example 1-2 | Ala-Hyp | 1.2 |
| Comparative Example 3 | Ser-Hyp | 0.7 |

<Evaluation Test 1-6>

C57BL/6J mice of an age of 10 weeks were caused to orally ingest feeds having compositions as shown in Table 7 below.

TABLE 7

| | N group | C group | Hyp-Gly-added group | [(Hyp-Gly) + (Pro-Hyp)]-added group | (Pro + Hyp)-added group |
|---|---|---|---|---|---|
| Casein | 200 | 200 | 200 | 200 | 200 |
| Lard | 58.3 | 58.3 | 58.3 | 58.3 | 58.3 |
| Corn oil | 11.7 | 11.7 | 11.7 | 11.7 | 11.7 |
| Mineral mixture | 35 | 35 | 35 | 35 | 35 |
| Vitamin mixture | 10 | 10 | 10 | 10 | 10 |
| Sucrose | 100 | 100 | 100 | 100 | 100 |
| Corn starch | 529.5 | 470.45 | 517.45 | 517.45 | 517.45 |
| Cellulose | 50 | 50 | 50 | 50 | 50 |
| L-Cystine | 3 | 3 | 3 | 3 | 3 |
| Potassium phosphate | — | 59.05 | 59.05 | 59.05 | 59.05 |
| Hyp-Gly | — | — | 3 | 1.5 | — |
| Pro-Hyp | — | — | — | 1.5 | — |
| (Pro + Hyp) | — | — | — | — | 3 |

In this test, in Table 7, Hyp-Gly ([Hyp-Gly] group) was used as the Hyp-Gly-added group, and a 1:1 mixture of Hyp-Gly and Pro-Hyp ([(Hyp-Gly)+(Pro-Hyp)] group) was used as the [(Hyp-Gly)+(Pro-Hyp)]-added group. The mice was killed after 3 weeks, and the width of the articular cavity was measured from a µCT (desk micro CT scanner SKYSCAN 1172, produced by SKYSCAN) image of articular part between femur and tibia of each group, and the matrix structure and the state of cells were evaluated from non-decalcified hematoxylin-dyed cut specimens. For comparison, a free amino acid mixture-added group ([Pro+Hyp] group) where a free amino acid mixture of proline and hydroxyproline was used was used as the (Pro+Hyp)-added group in Table 7 to carry out the same procedure and evaluation.

The results are shown in Table 8.

TABLE 8

| | N group | C group | Example 1 [Hyp-Gly] group | Example 2 [(Hyp-Gly) + (Pro-Hyp)] group | [Pro + Hyp] group |
|---|---|---|---|---|---|
| Relative thickness of articular cartilage | 1.0 ± 0.2 | 0.5 ± 0.1(*) | 1.0 ± 0.2 | 1.0 ± 0.1 | 0.5 ± 0.2(*) |
| Pathologic scores (articular cartilage part) | 0.2 ± 0.04 | 5.0 ± 1.5(*) | 0.3 ± 0.05 | 0.2 ± 0.06 | 5.0 ± 1.8(*) |
| Feature of pathologic findings in articular cancelious bone part in comparison with N group | — | Remarkable decrease of bone volume. Remarkable decrease of osteoblasts and bone cells; to the contrary, increase of number of osteoclasts | The same bone volume as N group. The same number of osteoblasts and bone cells as N group exist. | The same bone volume as N group. The same number of osteoblasts and bone cells as N group exist. | Bone volume decreased more than N group. Decrease of number of osteoblasts and bone cells. |

Number of tested animals: n = 4
Note)
(*)There is statistically a significant difference in comparison with N group. ($p < 0.05$)

<Evaluation Test 1-7>

Each of Hyp-Gly alone ([Hyp-Gly] group) and a 1:1 mixture of Hyp-Gly and Pro-Hyp ([(Hyp-Gly)+(Pro-Hyp)] group) was solubilized in physiological saline so as to be 5 mmol/L in end concentration and then subjected to filtration sterilization. An amount of 0.5 mL of the resultant solution was injected into an articular cavity between left femur and tibia of C group where C57BL/6J mice of an age of 10 weeks had been given feeds having compositions of Table 7 above for 3 weeks. After 1 week, the mice were killed, and non-decalcified Mayer hematoxylin-dyed cut specimens of articular cavity parts between right and left femur and tibia were prepared and subjected to pathologic evaluation. In the same way, also as to cases where the mice were killed after 3 weeks from the injection, non-decalcified Mayer hematoxylin-dyed cut specimens of articular cavity parts between right and left femur and tibia were prepared and subjected to pathologic evaluation by comparison with pathologic cut specimens of N group in the aforementioned evaluation test 1-6.

The results are shown in Table 9.

<Consideration of Results of Performance Evaluation Tests>

As seen in the above results, from comparison with the controls (blanks), it can be understood that: the Hyp-Gly inhibits the differentiation of activation of osteoclasts (Table 1), promotes the differentiation of activation of osteoblasts (Table 2), inhibits the degeneration of cartilage cells to adjust their differentiation (Table 3), and recovers the amount of tropocollagen in skin dermis (Table 5). In addition, these effects are more excellent than those of the other dipeptides, amino acids and tripeptide according to the comparative examples.

In addition, it can be understood that the Hyp-Gly is absorbed into intestine extremely rapidly and stably (without being decomposed into amino acids), when compared with the Ser-Hyp and the Ala-Hyp (Table 6).

In addition, from the results as shown in Tables 8 and 9, it can be understood that in the cases of the single use of Hyp-Gly being the dipeptide according to the present invention or in the cases of its joint use with Pro-Hyp, the degeneration of articular cartilages is inhibited or the regeneration of articular cartilages is promoted.

TABLE 9

| | | Example 1 [Hyp-Gly] group | | Example 2 [(Hyp-Gly) + (Pro-Hyp)] group | |
|---|---|---|---|---|---|
| | N group | 1 week after injection | 3 weeks after injection | 1 week after injection | 3 weeks after injection |
| Relative thickness of articular cartilage | 1.0 ± 0.2 | 0.8 ± 0.2 | 1.0 ± 0.1 | 0.9 ± 0.1 | 1.0 ± 0.05 |
| Pathologic scores (articular cartilage part) | 0.2 ± 0.04 | 0.4 ± 0.04 | 0.2 ± 0.03 | 0.3 ± 0.05 | 0.2 ± 0.02 |
| Feature of pathologic findings in articular cancelious bone part in comparison with N group | — | Increase of bone volume is seen. Many osteoblasts exist. | The same bone volume as N group. The same number of osteoblasts and bone cells as N group exist. | Remarkable increase of bone volume. Many osteoblasts exist. | The same bone volume as N group. The same number of osteoblasts and bone cells as N group exist. |

Number of tested animals: n = 4

Furthermore, in the cases of the joint use of Hyp-Gly and Pro-Hyp, it can be understood that effects more than expected from effects of their respective single use are displayed, and their synergistic effects are recognized (Tables 1 to 3 and 5). Particularly, in the promotion of activation of osteoblasts (Table 2) and the inhibition of degeneration of cartilage cells (Table 3), effects more excellent than both of the single use of Hyp-Gly and the single use of Pro-Hyp are displayed.

As to the inhibition of degeneration of cartilage cells (Table 3), the cases of the triple joint use of Hyp-Gly, Pro-Hyp and Ala-Hyp display effects more excellent than any other case, and remarkable synergistic effects by also using the Ala-Hyp jointly are recognized.

Incidentally, as to the Pro-Hyp, in the evaluation on a plastic Petri dish in Table 1 or in the evaluation of "relative value (%) of ALP" in Table 2, remarkable effects like the Hyp-Gly are not recognized. However, from the evaluation on dentin slices in Table 1, it is clear that the Pro-Hyp is effective for the inhibition of differentiation and activation of osteoclasts, and therefore it can be understood that the Pro-Hyp is effective for the inhibition of osteoporosis. Furthermore, as seen in Table 3, it can be understood that the Pro-Hyp is excellent also in the effect to inhibit the degeneration of cartilage cells.

From the results as shown in Table 3, it can also be understood that the Ala-Hyp standing alone is effective for the inhibition of degeneration of cartilage cells.

In addition, it can be understood that similarly to the Hyp-Gly, the Pro-Hyp is absorbed into intestine extremely rapidly and stably (without being decomposed into amino acids), when compared with the Ser-Hyp and the Ala-Hyp (Table 6).

[Malady Inhibitors]

Malady inhibitors according to the present invention were obtained using the above-mentioned dipeptides or collagen peptides according to the present invention. Examples of their compositions are hereinafter shown.

Examples 8 to 13

Ingredients were mixed in accordance with the compositions as shown in Table 10, and crystalline cellulose was used as a forming material in a ratio of 10 parts to the entirety of each composition as described in Table 10 to carry out tablet molding by a conventional method, thereby obtaining malady inhibitors according to Examples 8 to 13 usable by oral administration. Incidentally, in Table 10, the Hyp-Gly is the synthetic dipeptide of Example 1, the Pro-Hyp is the synthetic dipeptide of Referential Example 1-1, the PC, FC, PC-CP and PC-PH are the collagen peptides of Examples 4 to 7 respectively, and the PC-CP-Cont is the collagen peptide of Comparative Example 7.

TABLE 10

|  | Example 8 (weight %) | Example 9 (weight %) | Example 10 (weight %) | Example 11 (weight %) | Example 12 (weight %) | Example 13 (weight %) |
|---|---|---|---|---|---|---|
| Hyp-Gly | 2 | 1 | — | — | — | — |
| Pro-Hyp | — | 1 | — | — | — | — |
| PC | — | — | 76 | — | — | — |
| FC | — | — | — | 76 | — | — |
| PC-CP | — | — | — | — | 76 | — |
| PC-PH | — | — | — | — | — | 76 |
| PC-CP-Cont | 74 | 74 | — | — | — | — |
| Calcium (oyster shell calcination pulverization) | 6 | 6 | 6 | 6 | 6 | 6 |

TABLE 10-continued

|  | Example 8 (weight %) | Example 9 (weight %) | Example 10 (weight %) | Example 11 (weight %) | Example 12 (weight %) | Example 13 (weight %) |
|---|---|---|---|---|---|---|
| Glucosamine hydrochloride | 14 | 14 | 14 | 14 | 14 | 14 |
| Vitamin C | 4 | 4 | 4 | 4 | 4 | 4 |

Example 14

Chewable type tablets were produced using the above PC of Example 4.

Specifically, the below-mentioned ingredients were mixed to prepare chewable type tablets of 0.8 g per tablet using a tablet molding tool. These chewable type tablets contained Hyp-Gly as an effective component in a ratio of about 10.0 weight % when the entirety was assumed to be 100 weight %.

| PC | 50.0 kg |
|---|---|
| Ascorbic acid | 10.0 kg |
| MICROCALMAG S (produced by SK Foods) | 4.6 kg |
| MABIT (produced by Hayashibara) | 19.0 kg |
| Crystalline cellulose | 10.0 kg |
| Emulsifier | 3.2 kg |
| Aspartame | 0.5 kg |
| Fermented milk powder | 1.4 kg |
| Powder perfume | 1.0 kg |
| Citric acid | 0.3 kg |

Example 15

The PC of Example 4 was used, and the below-mentioned ingredients were mixed to prepare a powder clear soup (6.0 g per bag) for being drunken by dissolving it into 100 to 140 mL of hot water. This powder clear soup contained Hyp-Gly as an effective component in a ratio of about 7.0 weight % when the entirety was assumed to be 100 weight %.

| PC | 35.0 kg |
|---|---|
| Chicken essence powder | 25.0 kg |
| Table salt | 18.0 kg |
| Glucose | 7.7 kg |
| Calcium lactate | 7.0 kg |
| Sodium glutamate | 4.0 kg |
| Onion essence powder | 1.0 kg |
| HVP | 1.0 kg |
| Beef flavor | 0.5 kg |
| Disodium 5'-ribonucleotide | 0.5 kg |
| White pepper | 0.2 kg |
| Turmeric | 0.1 kg |

Example 16

The PC of Example 4 was used, and the below-mentioned ingredients were mixed to prepare a powder juice (13.0 g per bag) for being drunken by dissolving it into 100 to 150 mL of water. This powder juice contained Hyp-Gly as an effective component in a ratio of about 8.0 weight % when the entirety was assumed to be 100 weight %.

| | |
|---|---|
| PC | 40.4 kg |
| Sodium ascorbate | 1.2 kg |
| Erythritol | 52.0 kg |
| Acesulfame K | 0.1 kg |
| Aspartame | 0.1 kg |
| Sodium citrate | 0.8 kg |
| Citric acid (crystal) | 4.6 kg |
| Muscat flavor | 0.8 kg |

Example 17

The PC of Example 4 was used, and following the below-mentioned ingredient composition, into purified water there were dissolved the other ingredients, and the resultant solution was adjusted to pH 3.5, B'×9.0% and then subjected to heat-sterilization treatment at 110° C. for 30 seconds and then cooled to 10° C. and then aseptically filled into a paper pack, thereby preparing a refreshing drink (125 mL per pack). This refreshing drink contained Hyp-Gly as an effective component in a ratio of about 0.5 weight % when the entirety was assumed to be 100 weight %.

| | |
|---|---|
| PC | 2.5 kg |
| Vitamin mix DN (produced by BASF, Japan) | 0.1 kg |
| Erythritol | 5.5 kg |
| Acesulfame K | 0.015 kg |
| Aspartame | 0.005 kg |
| Citric acid | about 0.6 kg |
| Fruits mix flavor | 0.16 L |
| Litchi flavor | 0.04 L |
| Purified water | balance |

(The balance was set so that the total would be 100.0 kg)<

Example 18

First of all, the PC of Example 4 and gelatin were immersed into purified water (B) among the below-mentioned ingredients and thereby swollen for 30 minutes and then completely dissolved by heating to 80° C. for 30 minutes, thereby obtaining a gelatin solution. Next, milk oligosaccharide, powder malt reducing sugar, erythritol and intractably digestible dextrin were dissolved into purified water (A) among the below-mentioned ingredients and boiled down, and then thereto aspartame, the aforementioned gelatin solution, citric acid (crystal) as beforehand dissolved into part of the purified water (A), peppermint flavor, mint flavor, lemon flavor and safflower yellow color were added, and the resultant solution was adjusted to B'×79 to 81% and then defoamed and then filled into a starch mold and then dried at room temperature for 24 hours, thereby preparing a gummy jelly (4 g per grain). This gummy jelly contained Hyp-Gly as an effective component in a ratio of about 1.0 weight % when the entirety was assumed to be 100 weight %.

| | |
|---|---|
| PC | 5.0 kg |
| Milk oligosaccharide | 41.0 kg |
| Powder malt reducing sugar | 31.0 kg |
| Erythritol | 5.0 kg |
| Intractably digestible dextrin | 5.0 kg |
| Aspartame | 0.05 kg |
| Gelatin (APH250, produced by Nitta Gelatin, Inc.) | 7.0 kg |
| Citric acid (crystal) | 1.2 kg |
| Peppermint flavor | 0.6 L |

-continued

| | |
|---|---|
| Mint flavor | 0.2 L |
| Lemon flavor | 0.7 L |
| Safflower yellow color | proper amount |
| Purified water (A) | 20.0 L |
| Purified water (B) | 18.0 L |

Example 19

The Hyp-Gly of Example 1 was solubilized with sterilized physiological saline so as to be 2.5 mM in concentration, thereby obtaining a malady inhibitor according to Example 19 usable by injection into a diseased part.

—Referential Data Relating to Pro-Hyp—

Hereinafter, for reference, effects of Pro-Hyp-containing collagen peptides and Pro-Hyp are shown.

First of all, the Pro-Hyp-containing collagen peptides as used in the performance evaluation tests are explained. As the collagen peptides, there were prepared two kinds of Pro-Hyp-containing pig skin-derived collagen peptides (hereinafter abbreviated as "PC" and "PC-CA" respectively), a Pro-Hyp-containing fish scale-derived collagen peptide according to the present invention (hereinafter abbreviated as "FC") and, for comparison, two kinds of Hyp-Gly and Pro-Hyp-free pig skin-derived collagen peptides (hereinafter abbreviated as "PC-Cont" and "PC-CA-Cont" respectively).

<PC>

An amount of 1 kg of gelatin (I type collagen) being a heat-degenerated product of a pig skin-derived collagen was dissolved into 4 kg of 75° C. warm water, and its temperature was adjusted to 60° C., and thereafter as a primary enzymatic reaction, 10 g of yellow Aspergillus-derived protease was added, and the system was kept at a pH of 5.0 to 6.0 and a temperature of 45 to 55° C. for 120 minutes, thereby carrying out an enzymatic hydrolysis treatment. Next, as a secondary enzymatic reaction, an Aspergillus oryzae-extracted enzyme having aminopeptidase P and prolidase activity was added so as to be 0.5% in end concentration, so that the material was made soluble. Thereafter, the material was reacted at 50° C. for 6 hours. After the reaction, the reaction liquid was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC was obtained.

This PC was subjected to thin-layer chromatography. That is to say, 10 μg of the water-solubilized PC was dropped onto a thin-layer chromatography plate (trade name: "Cellulose F", produced by Merck) and then eluted with a solvent (n-butanol:acetic acid:water=4:1:2). This plate was air-dried and then sprayed with an isatin-zinc acetate reagent, and thereafter the presence of a peptide of which the N terminal end was Pro was confirmed by a blue spot, and it was also confirmed that the Rf value {[distance from spot original to colored spot]/[distance from spot original to solvent front]} of the blue spot of the above-obtained PC consisted with the Rf value of each blue spot of the Pro-Hyp among the Hyp-Gly and the Pro-Hyp which were internal markers spotted to the same plate, in other words, this PC contained the Pro-Hyp.

<FC>

An FC was obtained in the same way as of the aforementioned production of the PC except that a fish scale-derived gelatin was used.

In addition, this FC was analyzed by thin-layer chromatography in the same way as of the aforementioned case of the PC. As a result, the presence of Pro-Hyp was confirmed.

<PC-CA>

An amount of 1 kg of gelatin (I type collagen) being a heat-degenerated product of a pig skin-derived collagen was dissolved into 4 L of 20 mM tris-HCl buffer (pH 7.5) of 75° C. while heated and then cooled to 40° C., and thereafter as a primary enzymatic reaction, 1 g of collagenase (Collagenase N-2, produced by Nitta Gelatin, Inc.) was added, and the system was kept at a pH of 7.0 to 7.8 and a temperature of 40° C. for 24 hours, thereby carrying out an enzymatic decomposition treatment. Next, as a secondary enzymatic reaction, an *Aspergillus niger*-extracted enzyme having aminopeptidase P and prolidase activity was added to the resultant reaction liquid so as to be 0.25% in end concentration. Thereafter, the material was reacted at pH 4.0 and 50° C. for 6 hours. After the reaction, the reaction liquid was subjected to heat treatment at 100° C. for 10 minutes and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC-CA was obtained.

A solution prepared by dissolving 2 g (dry weight) of the aforementioned PC-CA into 10 mL of water were separated into two, and they were sequentially charged into a column ("DEAE TOYOPEARL 650M", produced by TOSOH Corporation; 16×650 mm), and a void volume fraction eluted with distilled water was recovered. Next, the recovered fraction was charged into a column ("SP TOYOPEARL 650M", produced by TOSOH Corporation; 16×650 mm), and a void volume fraction eluted with distilled water was recovered. Next, this fraction was charged into a column ("SEPHADEX LH-20", produced by Pharmacia Co., Ltd.; 26×900 mm), and elution was made with a 30% aqueous methanol solution. Fractionation was made at 9 mL/fraction, so that a fraction corresponding to a position where the Pro-Hyp which was a chemical synthetic product was eluted was recovered. This fraction was provided to an HPLC using a column ("µBondasphere 5 µC18 300 Å", produced by Waters Co., Ltd.; 3.9×150 mm) to make fractionation by a linear concentration gradient elution of a 0 to 32% or less aqueous acetonitrile solution containing 0.1% trifluoroacetic acid (carried out at a flow rate of 1 mL/min and a gradient of 0 to 32% in 18 minutes), so that a peak part eluted at a retention time corresponding to a position where the Pro-Hyp which was a chemical synthetic product was eluted was recovered. Then, the recovered liquid was vacuum-dried to solid, so that a white powder was obtained. The structure of the obtained white powder was analyzed with a protein structure analyzer ("Protein Sequencer 491 Model", produced by Applied Biosystems) by the Edman method. As a result, the presence of Pro-Hyp was confirmed.

<PC-Cont>

A PC-Cont was obtained by carrying out only the primary enzymatic reaction in the aforementioned production of the PC.

That is to say, 1 kg of gelatin (I type collagen) being a heat-degenerated product of a pig skin-derived collagen was dissolved into 4 kg of 75° C. warm water, and its temperature was adjusted to 60° C., and thereafter 10 g of yellow *Aspergillus*-derived protease was added, and the system was kept at a pH of 5.0 to 6.0 and a temperature of 45 to 55° C. for 120 minutes, thereby carrying out an enzymatic hydrolysis treatment. Next, a solution obtained by the enzymatic hydrolysis treatment was heated at 85° C. for 10 minutes to deactivate the enzyme and then cooled to 60° C. and then filtered with active carbon and a filtration assistant (diatomite), and the resultant mother liquor was subjected to high-temperature sterilization treatment at 120° C. for 3 seconds. Then, the sterilized mother liquor was spray-dried, so that a PC-Cont was obtained.

In addition, this PC-Cont was analyzed by thin-layer chromatography in the same way as of the aforementioned case of the PC. As a result, no blue spot was seen, so that the presence of any of the Hyp-Gly and the Pro-Hyp could not be confirmed.

<PC-CA-Cont>

A PC-CA-Cont was obtained by carrying out only the primary enzymatic reaction in the aforementioned production of the PC-CA.

That is to say, 1 kg of gelatin (I type collagen) being a heat-degenerated product of a pig skin-derived collagen was dissolved into 4 L of 20 mM tris-HCl buffer (pH 7.5) of 75° C. while heated and then cooled to 40° C., and thereafter 1 g of collagenase (Collagenase N-2, produced by Nitta Gelatin, Inc.) was added, and the system was kept at a pH of 7.0 to 7.8 and a temperature of 40° C. for 24 hours, thereby carrying out an enzymatic decomposition treatment. Next, a solution obtained by the enzymatic hydrolysis treatment was heated at 85° C. for 10 minutes to deactivate the enzyme and then filtered with active carbon and a filtration assistant (diatomite), and the resultant mother liquor was subjected to high-temperature sterilization treatment at 120° C. for 3 seconds. Then, the sterilized mother liquor was spray-dried, so that a powdered PC-CA-Cont was obtained.

In addition, this PC-CA-Cont was analyzed by thin-layer chromatography in the same way as of the aforementioned case of the PC. As a result, no blue spot was seen, so that the presence of any of the Hyp-Gly and the Pro-Hyp could not be confirmed.

<Evaluation Test 2-1>

The aforementioned PC (PC group), FC (FC group) and PC-CA (PC-CA group) were used, and each collagen peptide was added to a precursory cartilage cell stock ATDC5 culture liquid so as to be 0.1% in end concentration. After 5 days from the culture, each inhibition activity of alkaline phosphatase (ALP) being a marker enzyme for hypertrophied cartilages and calcification was examined. For comparison, the ALP inhibition activity when adding no peptide (N group), the ALP inhibition activity when using peptone (Pe group) of 0.1% in end concentration, and the ALP inhibition activity when using the aforementioned PC-Cont (PC-Cont group) and PC-CA-Cont (PC-CA-Cont group) were also examined. The results are shown in Table 11.

TABLE 11

| | N group | Pe group | PC group | FC group | PC-CA group | PC-Cont group | PC-CA-Cont group |
|---|---|---|---|---|---|---|---|
| Relative ALP activity | 1.0 ± 0.01 | 1.2 ± 0.01 | 0.3 ± 0.05(*) | 0.7 ± 0.05(*) | 0.2 ± 0.05(*) | 0.9 ± 0.1 | 0.9 ± 0.15 |

(*)There is seen statistically a significant difference in comparison with N group. (p < 0.05)

<Evaluation Test 2-2>

The ALP inhibition activity was examined in the same way as of evaluation test 2-1 except that: a dipeptide Pro-Hyp as synthesized by a solid-phase method (produced by PH Japan) ([Pro-Hyp] group) was used, the amount of its addition was changed to 2.5 mM and, for comparison, no peptide was added (N group) or glycine being a free amino acid (Gly group), proline being a free amino acid (Pro group), hydroxyproline being a free amino acid (Hyp group), a free amino acid mixture of proline and hydroxyproline ([Pro+Hyp] group), a free amino acid mixture of glycine, proline and hydroxyproline ([Gly+Pro+Hyp] group), and a tripeptide Pro-Hyp-Gly as synthesized by a solid-phase method (produced by PH Japan) ([Pro-Hyp-Gly] group) were used. The results are shown in Table 12.

TABLE 12

|  | N group | Gly group | Pro group | Hyp group | [Pro + Hyp] group | [Gly + Pro + Hyp] group | [Pro-Hyp] group(**) | [Pro-Hyp-Gly-] group |
|---|---|---|---|---|---|---|---|---|
| Relative ALP activity | 1.0 ± 0.1 | 1.1 ± 0.01 | 0.98 ± 0.1 | 1.0 ± 0.01 | 1.0 ± 0.03 | 1.0 ± 0.01 | 0.1 ± 0.02(*) | 0.8 ± 0.01 |

(*)There is seen statistically a significant difference in comparison with N group.
(**)Produced by PH Japan <Evaluation Test 2-3>

C57BL/6J mice of an age of 10 weeks were caused to orally ingest feeds having compositions as shown in Table 13. In this test, in Table 13, the aforementioned PC (PC group), FC (FC group) and PC-CA (PC-CA group) were used as collagen peptide-added groups, and for comparison, the aforementioned PC-Cont (PC-Cont group) and PC-CA-Cont (PC-CA-Cont group) were used. The mice was killed after 3 weeks, and from non-decalcified hematoxylin-dyed cut specimens of articular part between femur and tibia of each group, the matrix structure and the state of cells were evaluated and the width of the articular cavity was measured.

The results are shown in Tables 14 and 16. The values as shown in Table 14 (pathologic scores) are values obtained by evaluating the matrix structure and state of cells of articular cartilage of each mouse on the criteria as shown in Table 15 and averaging the evaluation values.

TABLE 13

|  | N group | C group | Collagen peptide-added group | Pro-Hyp-added group | (Pro + Hyp)-added group |
|---|---|---|---|---|---|
| Casein | 200 | 200 | 150 | 200 | 200 |
| Lard | 58.3 | 58.3 | 58.3 | 58.3 | 58.3 |
| Corn oil | 11.7 | 11.7 | 11.7 | 11.7 | 11.7 |
| Mineral mixture | 35 | 35 | 35 | 35 | 35 |
| Vitamin mixture | 10 | 10 | 10 | 10 | 10 |
| Sucrose | 100 | 100 | 100 | 100 | 100 |
| Corn starch | 529.5 | 470.45 | 470.45 | 517.45 | 517.45 |
| Cellulose | 50 | 50 | 50 | 50 | 50 |
| L-Cystine | 3 | 3 | 3 | 3 | 3 |
| Potassium phosphate | — | 59.05 | 59.05 | 59.05 | 59.05 |

TABLE 13-continued

|  | N group | C group | Collagen peptide-added group | Pro-Hyp-added group | (Pro + Hyp)-added group |
|---|---|---|---|---|---|
| Collagen peptide | — | — | 50 | — | — |
| Pro-Hyp | — | — | — | 3 | — |
| (Pro + Hyp) | — | — | — | — | 3 |

TABLE 14

|  | N group | C group | PC group | FC group | PC-CA group | PC-Cont group | PC-CA-Cont group |
|---|---|---|---|---|---|---|---|
| Pathologic scores (articular cartilage part) | 0.2 ± 0.04 | 5.0 ± 1.5(*) | 1.7 ± 0.5(*) | 2.0 ± 0.4(*) | 0.5 ± 0.5 | 2.3 ± 0.4(*) | 2.2 ± 0.4(*) |

(*)There is seen statistically a significant difference in comparison with N group. (p < 0.05)

TABLE 15

| Structure of matrix | | State of cells | |
|---|---|---|---|
| 0 | Ordinary | 0 | Ordinary |
| 1 | Surface extraordinary | 2 | Defect |
| 3 | Surface fiber spasticity | 5 | Strong defect |
| 6 | Deep cracks | 8 | Defect of entirety of cartilage and cells |
| 8 | Complete defect of cartilage | | |

TABLE 16

|  | N group | C group | PC group | FC group | PC-CA group | PC-Cont group | PC-CA-Cont |
|---|---|---|---|---|---|---|---|
| Relative thickness of articular | 1.0 ± 0.2 | 0.5 ± 0.1(*) | 0.9 ± 0.1 | 0.7 ± 0.2(*) | 1.0 ± 0.2 | 0.6 ± 0.2(*) | 0.6 ± 0.2(*) |

(*)There is seen statistically a significant difference in comparison with N group. ($p < 0.05$)

Furthermore, as to the aforementioned N group, C group and PC group, bone measurement by CT apparatus (X-ray CT Latheta, produced by ALOCA) was carried out. The results are shown in Table 17.

TABLE 17

|  | Total bone density ($mg/cm^3$) | Cortical bone density ($mg/cm^3$) | Cancelious bone density ($mg/cm^3$) | Total bone salt amount (mg) | Bone sectional secondary curvature moment (mg · cm) |
|---|---|---|---|---|---|
| N group | 617.57 ± 45.01 | 722.37 ± 43.66 | 418.10 ± 42.45 | 26.55 ± 2.05 | 0.142 ± 0.015 |
| C group | 550.10 ± 6.73 | 657.43 ± 10.78 | 350.28 ± 17.18 | 23.45 ± 1.09 | 0.113 ± 0.014 |
| PC group | 576.02 ± 24.67 | 682.00 ± 30.41 | 391.12 ± 27.44 | 27.17 ± 2.55 | 0.140 ± 0.017 |

<Evaluation Test 2-4>

C57BL/6J mice of an age of 10 weeks were caused to orally ingest feeds having compositions as shown in Table 13 above. In this test, in Table 13, a dipeptide Pro-Hyp being a chemically synthesized product (produced by BACHEM) ([Pro-Hyp] group) was used as the Pro-Hyp-added group. The mice was killed after 3 weeks, and the width of the articular cavity was measured from a μCT (desk micro CT scanner SKY-SCAN 1172, produced by SKYSCAN) image of articular part between femur and tibia of each group, and the matrix structure and the state of cells were evaluated from non-decalcified hematoxylin-dyed cut specimens. In addition, for comparison, a free amino acid mixture-added group ([Pro+Hyp] group) where a free amino acid mixture of proline and hydroxyproline was used was used as the (Pro+Hyp)-added group in Table 13 to carry out the same procedure and evaluation.

The results are shown in Table 18.

TABLE 18

|  | N group | C group | [Pro-Hyp] group | [Pro + Hyp] group |
|---|---|---|---|---|
| Relative thickness of articular cartilage | 1.0 ± 0.2 | 0.5 ± 0.1(*) | 0.9 ± 0.1 | 0.5 ± 0.2(*) |
| Pathologic scores (articular cartilage part) | 0.2 ± 0.04 | 5.0 ± 1.5(*) | 0.5 ± 0.5 | 5.0 ± 1.8(*) |
| Feature of pathologic findings in articular cancelious bone part in comparison with N group | — | Remarkable decrease of bone volume. Remarkable decrease of osteoblasts and bone cells; to the contrary, increase of number of osteoclasts | The same bone volume as N group. The same number of osteoblasts and bone cells as N group exist. | Bone volume decreased more than N group. Decrease of number of osteoblasts and bone cells. |

Number of tested animals: n = 4
Note)
(*)There is statistically a significant difference in comparison with N group. ($p < 0.05$)

<Evaluation Test 2-5>

A dipeptide Pro-Hyp as synthesized by a solid-phase method (produced by PH Japan) ([Pro-Hyp] group) was solubilized in physiological saline so as to be 5 mmol/L in end concentration and then subjected to filtration sterilization. An amount of 0.5 mL of the resultant solution was injected into an articular cavity between left femur and tibia of C group where C57BL/6J mice of an age of 10 weeks had been given feeds having compositions of Table 13 above for 3 weeks. After 1 week, the mice were killed, and non-decalcified Mayer hematoxylin-dyed cut specimens of articular cavity parts between right and left femur and tibia were prepared and subjected to pathologic evaluation. In the same way, also as to cases where the mice were killed after 3 weeks from the injection, non-decalcified Mayer hematoxylin-dyed cut specimens of articular cavity parts between right and left femur and tibia were prepared and subjected to pathologic evaluation by comparison with pathologic cut specimens of N group in the aforementioned evaluation test 2-4.

The results are shown in Table 19.

TABLE 19

|  | N group | [Pro-Hyp] group | |
|---|---|---|---|
|  |  | 1 week after injection | 3 weeks after injection |
| Relative thickness of articular cartilage | 1.0 ± 0.2 | 0.7 ± 0.1 | 1.0 ± 0.1 |
| Pathologic scores (articular cartilage part) | 0.2 ± 0.04 | 0.5 ± 0.05 | 0.2 ± 0.05 |
| Feature of pathologic findings in articular cancelious bone part in comparison with N group | — | There is a tendency for bone volume to increase. Many osteoblasts exist. | The same bone volume as N group. The same number of osteoblasts and bone cells as N group exist. |

Number of tested animals: n = 4

<Consideration of Results of Performance Evaluation Tests>

From the above results of evaluation tests 2-1 and 2-3 (Tables 11, 14 and 16), it can be understood that the Pro-Hyp-containing PC, FC and PC-CA display a more excellent effect to promote the regeneration of articular cartilages than the Hyp-Gly and Pro-Hyp-free PC-Cont and PC-CA-Cont.

In addition, in evaluation tests 2-2 and 2-4, the single use of Pro-Hyp being a synthetic dipeptide displays an excellent effect to promote the regeneration of articular cartilages. On the other hand, as to proline, hydroxyproline, glycine, their mixture, and Pro-Hyp-Gly, no effect to promote the regeneration of articular cartilages is seen (Tables 12 and 18).

Also in evaluation test 2-5, the single use of Pro-Hyp being a synthetic dipeptide displays an excellent effect to promote the regeneration of articular cartilages (Table 19).

[Malady Inhibitors]

Malady inhibitors were obtained using the above-mentioned Pro-Hyp or a collagen peptide containing it. For reference, examples of their compositions are hereinafter shown.

Referential Examples 2-1 to 2-3

Ingredients were mixed in accordance with the compositions as shown in Table 20, and crystalline cellulose was used as a forming material in a ratio of 10 parts to the entirety of each composition as described in Table 20 to carry out tablet molding by a conventional method, thereby obtaining malady inhibitors according to Referential Examples 2-1 to 2-3 usable by oral administration. Incidentally, in Table 20, the Pro-Hyp is the synthetic dipeptide produced by BACHEM as used in the above performance evaluation test, and the PC, PC-Cont and PC-CA-Cont are the collagen peptides as used in the above performance evaluation tests.

TABLE 20

|  | Example 2-1 (weight %) | Example 2-2 (weight %) | Example 2-3 (weight %) |
|---|---|---|---|
| Pro-Hyp | 4 | 4 | — |
| PC | — | — | 76 |
| PC-Cont | 72 | — | — |
| PC-CA-Cont | — | 72 | — |
| Calcium (oyster shell calcination pulverization) | 6 | 6 | 6 |
| Glucosamine hydrochloride | 14 | 14 | 14 |
| Vitamin C | 4 | 4 | 4 |

Referential Example 2-4

Chewable type tablets of 0.8 g per tablet were prepared in the same way as of Example 14 except that the Hyp-Gly-containing collagen peptide (PC) of Example 4 was replaced with the Pro-Hyp-containing collagen peptide (PC) as used in the above performance evaluation tests. These chewable type tablets contained Pro-Hyp as an effective component in a ratio of about 4.5 weight % when the entirety was assumed to be 100 weight %.

Incidentally, the sum (Y) of sequences of the Pro-Hyp being contained in a pig skin-derived I type collagen (weight (X) g) of which the amino acid sequence was already known was counted, and the theoretical content of the Pro-Hyp in the entirety of the I type collagen was determined from the following formula, so that it was 9.0 weight %.

((Number(Y) of Pro-Hyp)×(weight(molecular weight) of Pro-Hyp))/(weight(X) of all sequences)

From the above, it follows that the aforementioned PC contains the Pro-Hyp theoretically in a ratio of 9.0 weight % at the maximum.

The below-mentioned Referential Examples 2-5 to 2-8 are also examples of compositions in cases where the aforementioned PC containing the Pro-Hyp in a ratio of 9.0 weight % at the maximum was used for various uses in the same way as of the present Referential Example 2-4.

Referential Example 2-5

A powder clear soup (6.0 g per bag) for being drunken by dissolving it into 100 to 140 mL of hot water was prepared in the same way as of Example 15 except that the Hyp-Gly-containing collagen peptide (PC) of Example 4 was replaced with the Pro-Hyp-containing collagen peptide (PC) as used in the above performance evaluation tests. This powder clear soup contained Pro-Hyp as an effective component in a ratio of about 3.2 weight % when the entirety was assumed to be 100 weight %.

Referential Example 2-6

A powder juice (13.0 g per bag) for being drunken by dissolving it into 100 to 150 mL of water was prepared in the same way as of Example 16 except that the Hyp-Gly-containing collagen peptide (PC) of Example 4 was replaced with the Pro-Hyp-containing collagen peptide (PC) as used in the above performance evaluation tests. This powder juice contained Pro-Hyp as an effective component in a ratio of about 3.6 weight % when the entirety was assumed to be 100 weight %.

Referential Example 2-7

A refreshing drink (125 mL per pack) was prepared in the same way as of Example 17 except that the Hyp-Gly-containing collagen peptide (PC) of Example 4 was replaced with the Pro-Hyp-containing collagen peptide (PC) as used in the above performance evaluation tests. This refreshing drink contained Pro-Hyp as an effective component in a ratio of about 0.2 weight % when the entirety was assumed to be 100 weight %.

Referential Example 2-8

A gummy jelly (4 g per grain) was prepared in the same way as of Example 18 except that the Hyp-Gly-containing collagen peptide (PC) of Example 4 was replaced with the Pro-Hyp-containing collagen peptide (PC) as used in the above performance evaluation tests. This gummy jelly contained Pro-Hyp as an effective component in a ratio of about 0.45 weight % when the entirety was assumed to be 100 weight %.

Referential Example 2-9

Ingredients were mixed in accordance with the same composition as Referential Example 2-1 as shown in Table 20 except that none of PC-Cont, calcium and vitamin C was used. The resultant mixture was diluted to 5 mmol/L with physiological saline, thereby obtaining a malady inhibitor according to Referential Example 2-9 usable by injection into an articular local place.

INDUSTRIAL APPLICATION

Since the collagen peptide according to the present invention comprises a dipeptide which serves as an effective component of a malady inhibitor for prevention or curing of symptoms of such as osteoporosis, osteoarthritis and pressure ulcer, this collagen peptide can be used favorably as such as health foods and medicines having such functions.

The invention claimed is:

1. A method of inhibiting osteoporosis, osteoarthritis or pressure ulcer, comprising administering an effective amount of the dipeptide Hyp-Gly to a patient in need thereof.

2. A method of inhibiting osteoporosis or osteoarthritis, comprising administering an effective amount of the dipeptide Hyp-Gly to a patient in need thereof.

3. The method according to claim 1, comprising administrating further an effective amount of at least one dipeptide selected from a group consisting of Pro-Hyp and Ala-Hyp.

4. The method according to claim 2, comprising administrating further an effective amount of at least one dipeptide selected from a group consisting of Pro-Hyp and Ala-Hyp.

5. The method according to claim 1, comprising administering further an effective amount of glucosamine and/or a salt thereof.

6. The method according to claim 1, wherein the administration is made orally or by injection into an articular local phase.

* * * * *